(12) United States Patent
Hou et al.

(10) Patent No.: US 7,745,392 B2
(45) Date of Patent: Jun. 29, 2010

(54) MULTI-VALENT GUANIDINIUM COMPOUNDS FOR ENHANCING MOLECULAR TRANSLOCATION ACROSS CELLULAR MEMBRANES AND EPITHELIAL TISSUES

(75) Inventors: Zheng Hou, San Diego, CA (US); Jian Liu, San Diego, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 805 days.

(21) Appl. No.: 11/525,512

(22) Filed: Sep. 21, 2006

(65) Prior Publication Data

US 2007/0078078 A1    Apr. 5, 2007

Related U.S. Application Data

(60) Provisional application No. 60/720,318, filed on Sep. 23, 2005.

(51) Int. Cl.
| | |
|---|---|
| A61K 31/155 | (2006.01) |
| A61K 31/395 | (2006.01) |
| A61K 38/08 | (2006.01) |
| A61K 38/12 | (2006.01) |
| C07C 279/00 | (2006.01) |
| C07K 7/06 | (2006.01) |
| C07K 7/64 | (2006.01) |

(52) U.S. Cl. ............................. 514/2; 514/11; 514/17; 514/183; 514/394; 514/634; 514/636; 530/321; 530/330; 530/345; 340/472; 340/474; 564/236

(58) Field of Classification Search ........................ None
See application file for complete search history.

(56) References Cited

U.S. PATENT DOCUMENTS

| | | | | |
|---|---|---|---|---|
| 5,637,623 | A * | 6/1997 | Goldin et al. ............... | 514/634 |
| 6,235,711 | B1 * | 5/2001 | Dutta .......................... | 514/11 |
| 2002/0107196 | A1 * | 8/2002 | Gupta ......................... | 514/12 |
| 2002/0131965 | A1 * | 9/2002 | Rothbard et al. .......... | 424/130.1 |
| 2003/0073807 | A1 * | 4/2003 | Wender et al. ............. | 530/317 |
| 2005/0119167 | A1 | 6/2005 | Abbenante et al. | |
| 2007/0104645 | A1 * | 5/2007 | Garlich et al. ............. | 424/1.11 |
| 2008/0221020 | A1 * | 9/2008 | Goodman et al. .......... | 514/12 |

FOREIGN PATENT DOCUMENTS

| | | |
|---|---|---|
| WO | WO 02065986 | 8/2002 |
| WO | WO 02069930 | 9/2002 |
| WO | WO 03049772 | 6/2003 |
| WO | WO 2005/025513 | 3/2005 |
| WO | WO 2005/035549 | 4/2005 |
| WO | WO 2006/044063 | 4/2006 |

OTHER PUBLICATIONS

Edwards et al. Evaluation of Radiolabeled Type IV Collagen Fragments . . . Bioconjugate Chemistry. 2001, vol. 12, No. 6, pp. 1057-1065.*

Tamamura et al. Identification of Novel Low Molecular Weight CXCR4 Antagonists . . . Journal of Medicinal Chemistry. Apr. 13, 2005, vol. 48, No. 9, pp. 3280-3289.*

Zhang et al. "Solution- and Solid-Phase Syntheses of Guanidine-Bridged, Water-Soluble Linkers for Multivalent Ligand Design." Organic Letters. 2004, vol. 6, No. 9, pp. 1377-1380.*

Futaki et al., "Translocation of Branched-Chain Arginine Peptides through Cell Membranes: Flexibility in the Spatial Disposition of Positive Charges in Membrane-Permeable Peptides", *Biochemistry*, 2002, 41, 7925-7930.

Futaki, "Membrane-permeable arginine-rich peptides and the translocation mechanisms", *Advanced Drug Delivery Reviews 57*, 2005, 547-558.

Wright et al., "Guanidinium Rich Peptide Transporters and Drug Delivery", *Current Protein and Peptide Science*, 2003, 4, 105-124.

International Search Report for PCT/US2006/036746 dated May 14, 2007.

Written Opinion for PCT/US2006/036746 dated May 14, 2007.

Klein, "Hydrogen isotope effects in the reactions catalyzed by H2-forming N5,N10-methylenetetrahydromethanopterin dehydrogenase from methanogenic Archaea," Eur. J. Biochem., Oct. 1, 1995;233(1):372-376.

Office Action dated Oct. 17, 2008 in U.S. Appl. No. 11/525,482 filed Sep. 21, 2006.

Office Action dated Dec. 9, 2008 in U.S. Appl. No. 11/526,224 filed Sep. 22, 2006.

Diaz-Mochon et al., "Synthesis and cellular uptake of cell delivering PNA-peptide conjugates", *Chem. Commun.*, 2005, 3316-3318.

Dragulescu-Andrasi et al., "Cell-permeable GPNA with appropriate backbone stereochemistry and spacing binds sequence-specifically to RNA", *Chem. Commun.*, 2005, 2, 244-246.

Takahashi et al., "Design of a nucleobase conjugated peptide that recognizes HIV-1 RRE IIB RNA with high affinity and specificity", *Chem. Commun.*, 2002, 6:5, 349-350.

Zhou et al., "Novel Binding and Efficient Cellular Uptake of Guanidine-Based Peptide Nucleic Acids (GNPA)", *J. Am. Chem. Soc.*, 2003, 125:23, 6878-6879.

International Search Report for PCT/US2006/036743 dated Jul. 19, 2007.

Written Opinion for PCT/2006/036743 dated Jul. 19, 2007.

International Search Report for PCT/US2006/036745 dated Aug. 16, 2007.

Written Opinion for PCT/US2006/036745 dated Aug. 16, 2007.

Alm et al., "Effects of topically applied PGF2 alpha and its isopropylester on normal and glaucomatous human eyes", *Prog. Clin. Biol. Res.*, 1989, 312, 447-458.

Fuchs et al., "Pathway for Polyarginine Entry into Mammalian Cells Biochemistry", 2004, 43, 2438-2444.

(Continued)

*Primary Examiner*—Jeffrey E Russel
(74) *Attorney, Agent, or Firm*—Knobbe Martens Olson & Bear LLP

(57) ABSTRACT

Disclosed herein are guanidinium containing compounds consisting of a core moiety with a plurality of side chains containing guanidinium groups. Such compounds have enhanced translocation across cellular membranes and epithelial tissues. The compounds may also have a therapeutic or other biologically active moiety attached so that these moieties may be effectively transported into a cell by the guanidinium containing compound.

22 Claims, 1 Drawing Sheet

OTHER PUBLICATIONS

Jiang et al., "Tumor imaging by means of proteolytic activation of cell-penetrating peptides", *Proceedings of the National Academy of Sciences of USA*, 2004, 101, 17867-17872.

Joshi, "Microparticulates for ophthalmic drug delivery", *J. Ocul. Pharmacol.*, 1994, 10, 29-45.

Kirschberg et al., "Arginine-based molecular transporters: the synthesis and chemical evaluation of releasable taxol-transporter conjugates", *Organic Letters*, 2003, 5, 3459-3462.

Lagerholm et al., "Multicolor coding of cells with cationic peptide coated quantum dots", *Nano Letters American Chem. Soc. USA*, 2004, 4, 2019-2022.

Maiolo et al., "Effects of cargo molecules on the cellular uptake of arginine-rich cell-penetrating peptides", *Biochim. Biophys. Acta*, 2005, 1712, 161-172.

Mayer et al.,"Efficacy of a novel hydrogel formulation in human volunteers", *Ophthalmologica*, 1996, 210, 101-103.

Mordenti et al., "Intraocular pharmacokinetics and safety of a humanized monoclonal antibody in rabbits after intravitreal administration of a solution or a PLGA microsphere formulation", *Toxicol. Sci.*, 1999, 52, 101-106.

Rothbard et al., "Arginine-rich molecular transporters for drug delivery; role of backbone spacing in cellular uptake", *J. Medicinal Chem.*, 2002, 45, 3612-3618.

Shedden et al., "Efficacy and tolerability of timolol maleate ophthalmic gel-forming solution versus timolol ophthalmic solution in adults with open-angle glaucoma or ocular hypertension: a six-month, double-masked, multicenter study", *Clin. Ther.*, 2001, 23, 440-450.

Thomson et al., "Fmoc mediated synthesis of Peptide Nucleic Acids", *Tetrahedron*, 1995, 51(22), 6179-6194.

International Search Report for PCT/US2006/036746 dated Mar. 1, 2007.

Office Action dated Mar. 19, 2009 for U.S. Appl. No. 11/525,482, filed Sep. 21, 2006.

Office Action dated Jun. 11, 2009 for U.S. Appl. No. 11/525,482, filed Sep. 21, 2006.

Office Action dated Jun. 12, 2009 for U.S. Appl. No. 11/526,224, filed Sep. 22, 2006.

Notice of Allowability mailed Dec. 15, 2009 for U.S. Appl. No. 11/525,482, filed Sep. 21, 2006.

* cited by examiner

MULTI-VALENT GUANIDINIUM COMPOUNDS FOR ENHANCING MOLECULAR TRANSLOCATION ACROSS CELLULAR MEMBRANES AND EPITHELIAL TISSUES

RELATED APPLICATION

This application claims the benefit of U.S. Provisional Application No. 60/720,318, filed Sep. 23, 2005, which is incorporated herein by reference in its entirety.

SEQUENCE LISTING

The present application contains a Sequence Listing in electronic format. The Sequence Listing is provided as a file entitled NDTCO-042A-SEQUENCE-LISTING.TXT, created Mar. 11, 2009, which is 5 Kb in size. The information in the electronic format of the Sequence Listing is incorporated herein by reference in its entirety.

BACKGROUND OF THE INVENTION

1. Field of the Invention

The present invention relates to the fields of chemistry and medicine. More particularly, the present invention relates to guanidinium containing compounds that exhibit enhanced transmembrane transport of biologically active molecules.

2. Description of the Related Art

Protein transduction domains (PTD) are short cationic peptides that are capable of delivering molecules into mammalian cells. They include many diverse peptide sequences from many diverse sources. The phenomenon that peptide sequences can assist molecules across biological barriers is ubiquitous in biological systems. Such phenomenon can take place at different levels, including subcellular (e.g., nuclear membranes), cellular (e.g., cell membranes), and tissue levels (e.g., epithelial tissue). Sometimes the same peptide sequences can promote different translocation events at different biological levels.

SUMMARY OF THE INVENTION

A compound is disclosed having the formula:

Y—C—Z wherein C is a core moiety comprising an organic fragment having a molecular weight less than about 10,000;

wherein Y is a group of the formula:

T—(BB—G)$_n$—L— wherein about 2 to about 20 Y groups are attached to C;

wherein Z has the formula:

—L—T wherein one Z is attached to C or is absent;

wherein each L is separately selected to be a linker moiety comprising a molecular fragment having a molecular weight less than about 1000;

wherein each BB is separately selected to be a backbone moiety comprising an organic fragment having a molecular weight less than about 5000;

wherein each G is separately selected to be a guanidinium group covalently attached to a BB group and having the formula:

$$R^1N=C(NR^2)-N(R^3)(R^4)$$

wherein the point of attachment of G to BB is through a nitrogen atom or through $R^2$ or each G is separately selected from the group consisting of:

benzimidazol-2-ylidene-amine derivatives (as shown)

each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;

each $R^1$ is optionally bound to the $R^2$, $R^3$, or $R^4$ on the same guanidinium group to form a heterocyclic ring;

each $R^2$ is optionally bound to the $R^3$ or $R^4$ on the same guanidinium group to form a heterocyclic ring; and each $R^3$ is optionally bound to the $R^4$ on the same guanidinium group to form a heterocyclic ring;

wherein each T is a terminal group separately selected from the group consisting of hydrogen, an amine group, a carboxylic group, a N-terminal peptide or group that forms an N-terminal peptide bond with BB, a C-terminal peptide or group that forms a C-terminal peptide bond with BB, a reporting moiety, a targeting moiety, and a therapeutic moiety, or each T is separately absent; and wherein each n is separately selected to be an integer from 1 to 8.

In some embodiments, C is symmetric such as:
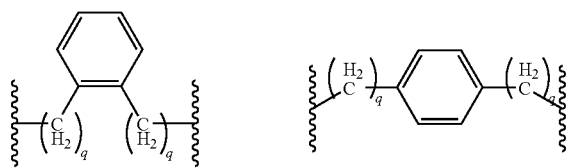
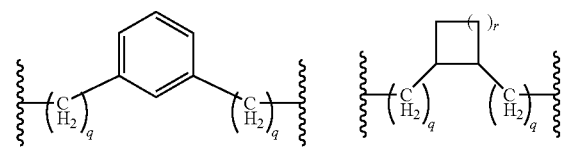
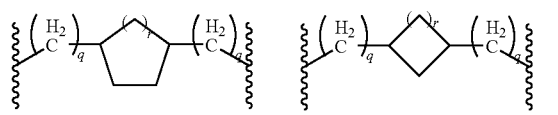
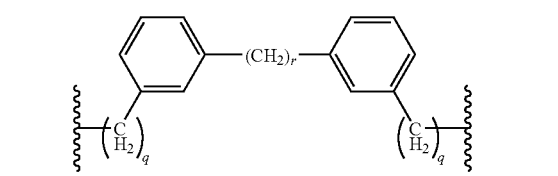
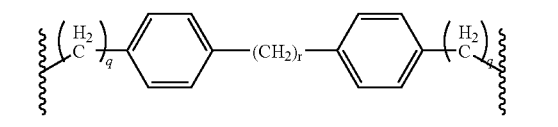
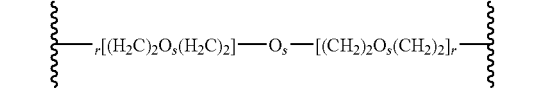
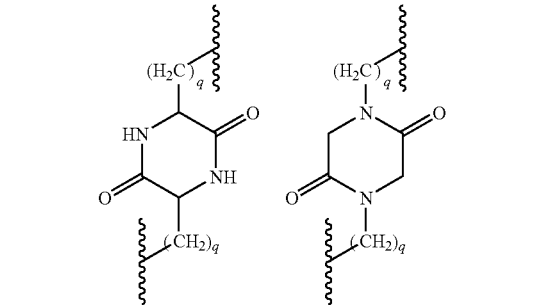
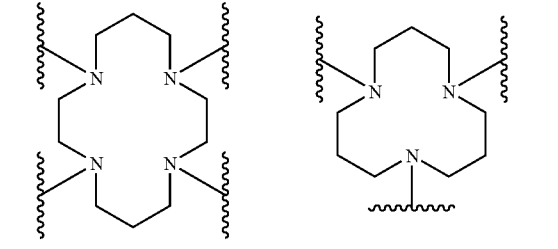
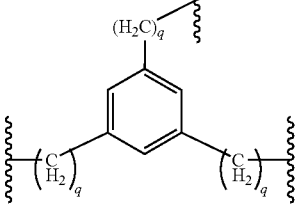
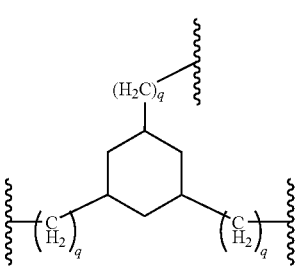
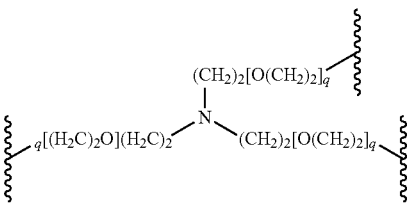
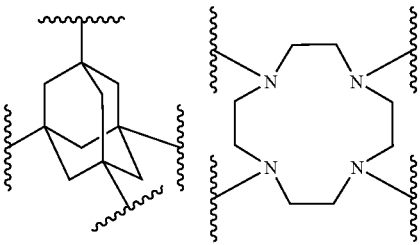
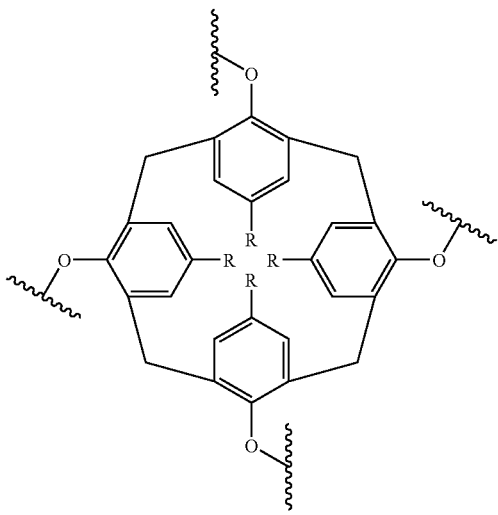

-continued

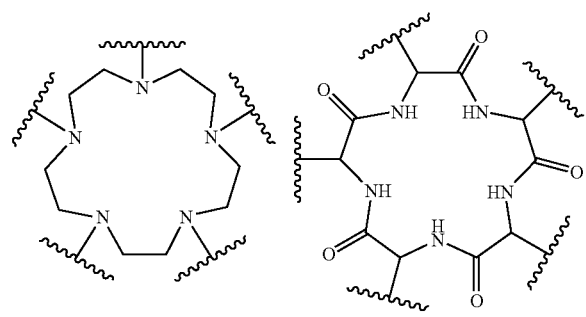

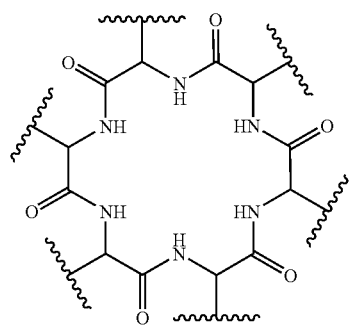

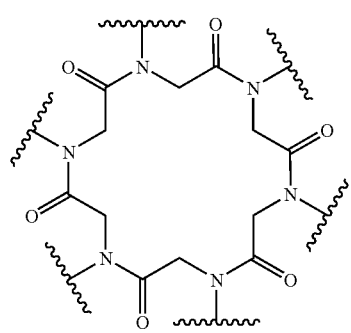

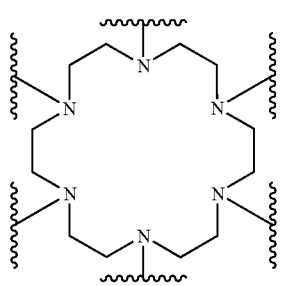

-continued

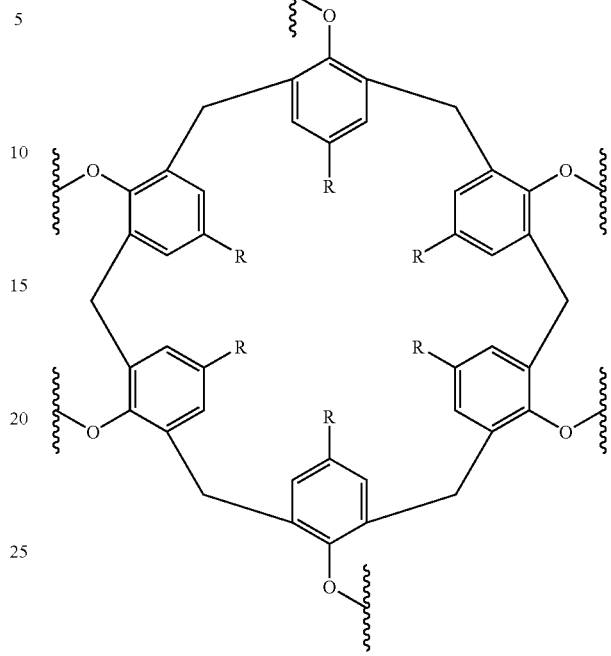

wherein:

q is an integer from 0 to 10;

r is an integer from 0 to 3;

s is an integer from 0 to 1; and

R is selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl.

In some embodiments, about 2 to about 6 Y groups are attached to C.

In some embodiments, each L is separately selected from the group consisting of: an oligopeptide comprising 1 to 12 amino acid residues, an optionally substituted $C_1$-$C_{12}$ alkyl, an optionally substituted $C_2$-$C_{12}$ alkenyl, an optionally substituted $C_2$-$C_{12}$ alkynyl, and an optionally substituted $C_{3-12}$ cyclic alkyl, alkenyl, alkynyl, or aromatic moiety.

In some embodiments, each L is separately selected from the group consisting of: —C(=O)NH—, —C(=O)NHO—, —C(=O)NHNH—, —S(=O)(=O)NR—, —P(=O)(—OR)NR'—, —SS—, —CH$_2$NR—, —CH$_2$NR—, —CH$_2$C(=O)NR—, —C(=O)O—, —C(=S)NR—, —S(=O)(=O)CH$_2$—, —SOCH$_2$— and —OC(=O)NR—, wherein each R and R' are separately selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl.

In some embodiments, at least two Y groups attached to C are different from each other.

In some embodiments, each BB-G is separately selected from the group consisting of:

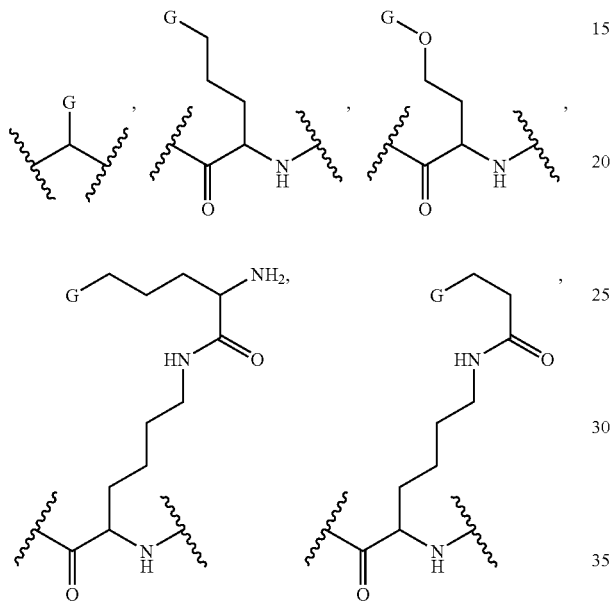
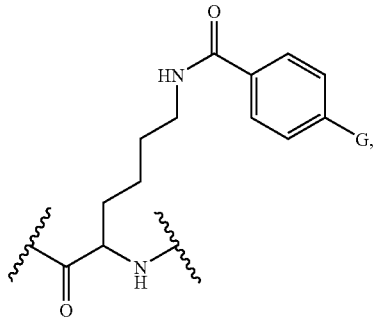
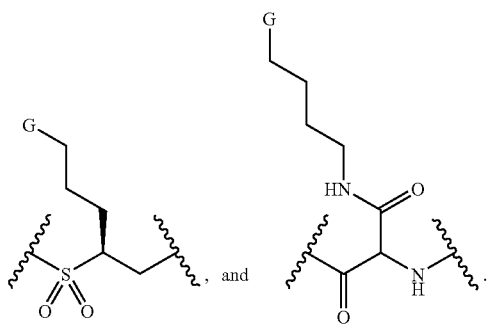

In various embodiments, at least one T comprises a polypeptide, protein antigen, tumor antigen, tisane moiety, antimicrobial agent, or cleavable linker, including cleavable linkers having an ester group or a disulfide group.

In some embodiments, $R^1$, $R^2$, $R^3$, and $R^4$ are hydrogen.

In some embodiments, the compound is selected from the group consisting of:

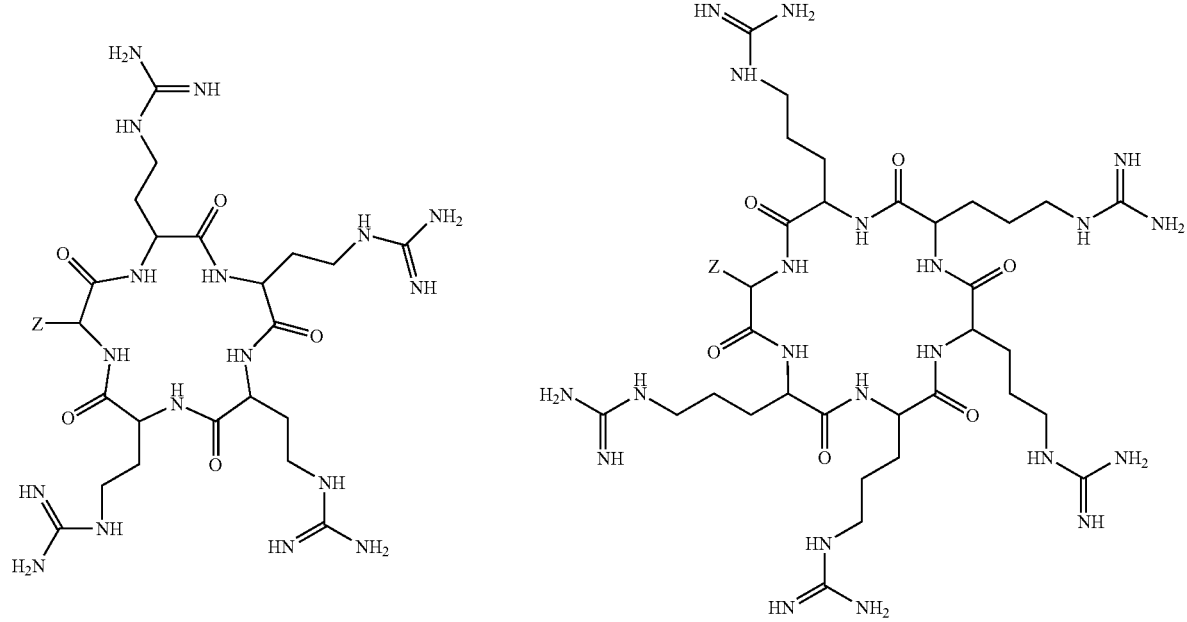

-continued
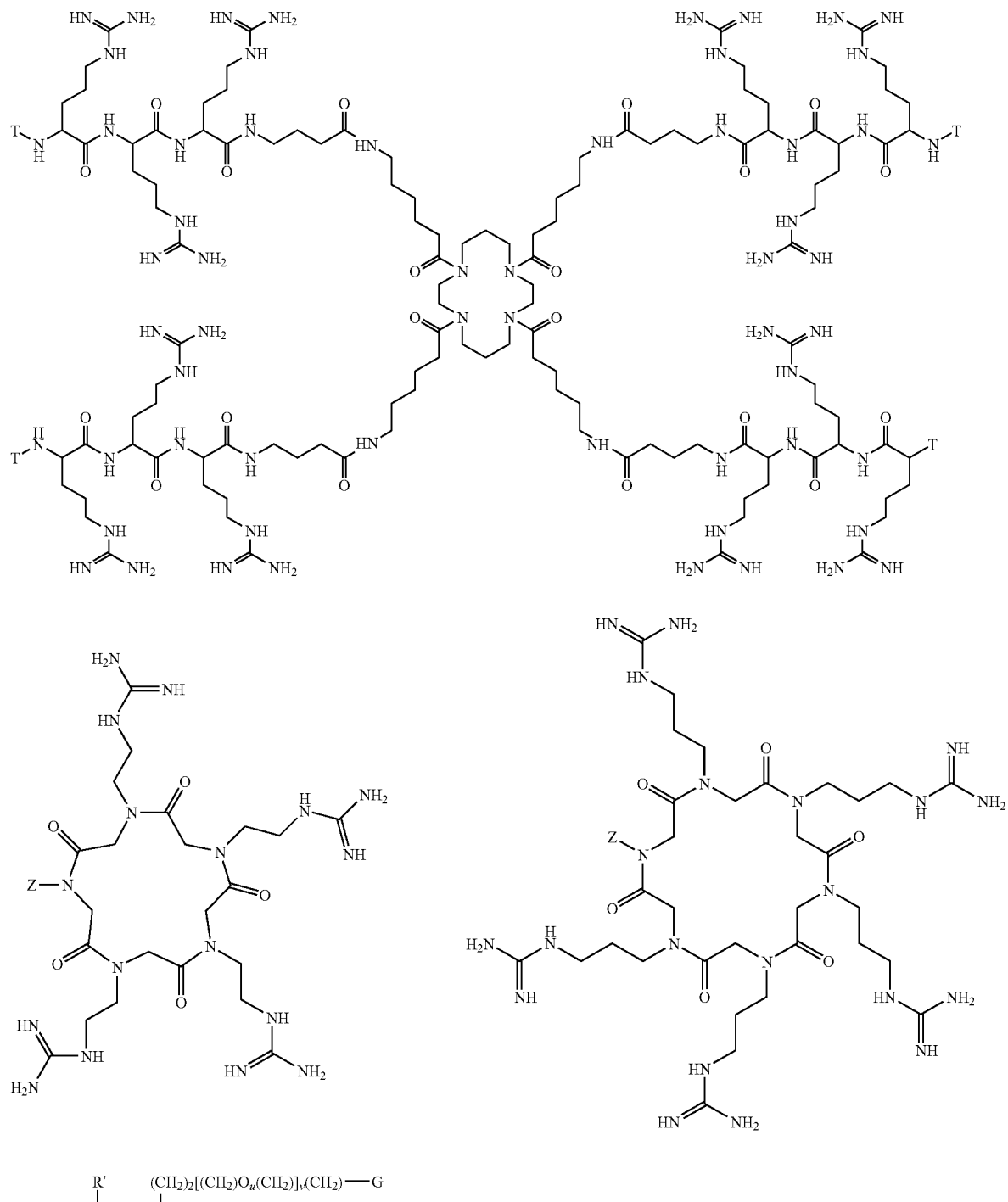
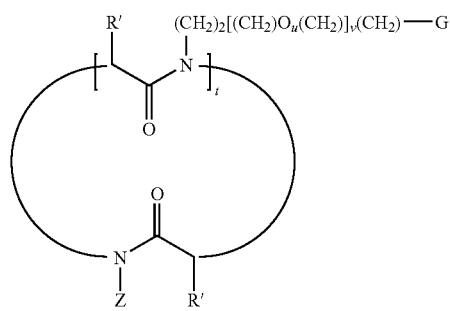

wherein t is an integer from about 1 to about 20;
u is an integer from 0 to 1;
t is an integer from about 1 to about 20;
v is an integer from about 0 to about 10; and
each R' is separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; amino; aminocarbonyl; aminocarboyloxy; nitro; azido; phenyl; hydroxy; alkylthio; arylthio; oxysulfonyl; carboxy; cyano; and halogenated alkyl including polyhalogenated alkyl.

Also disclosed herein is a compound having the formula:

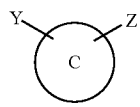

wherein C is selected from the group consisting of:

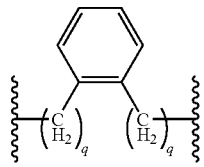 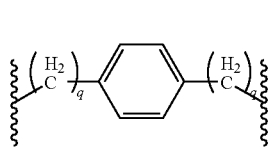

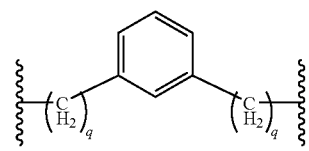 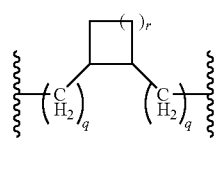

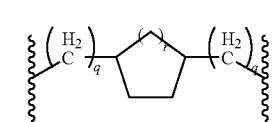 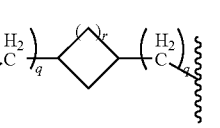

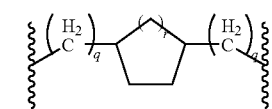 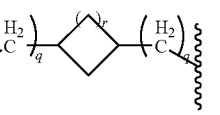

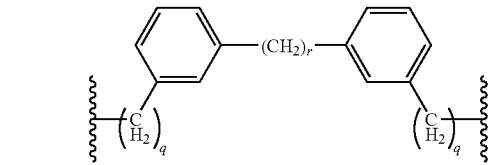

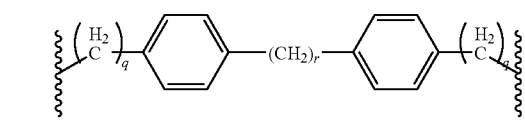

-continued

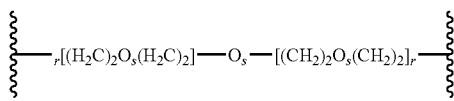

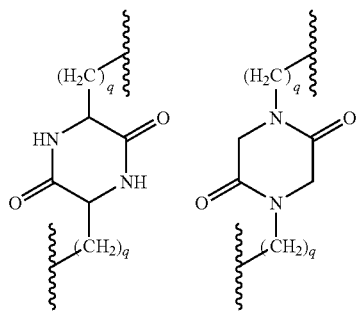

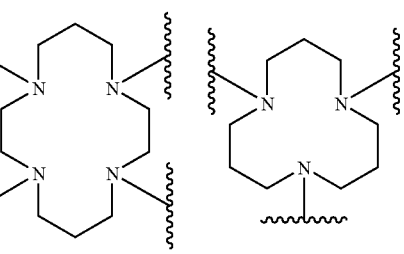

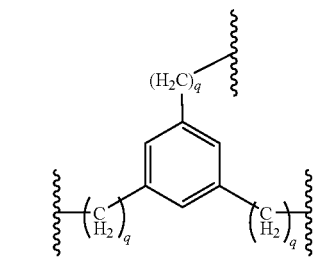

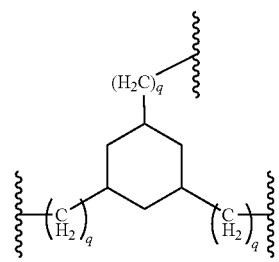

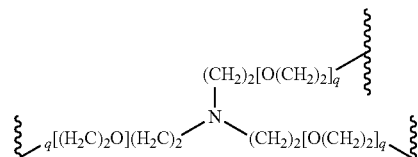

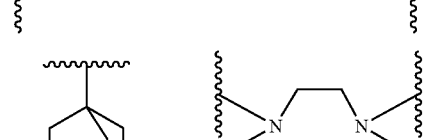

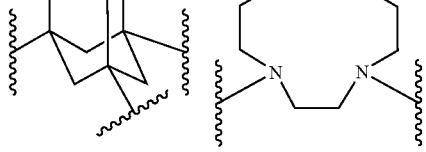

-continued
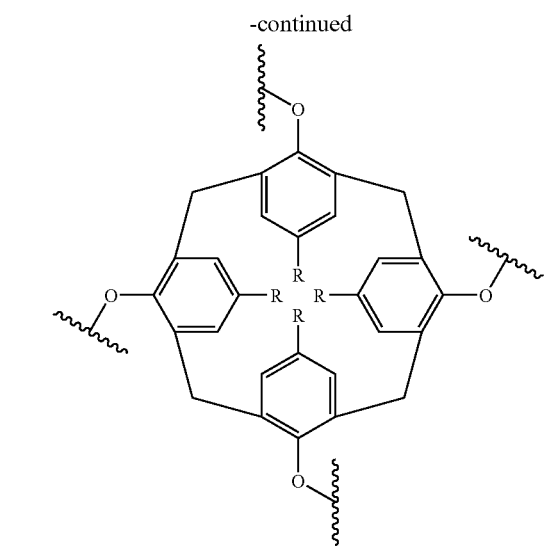
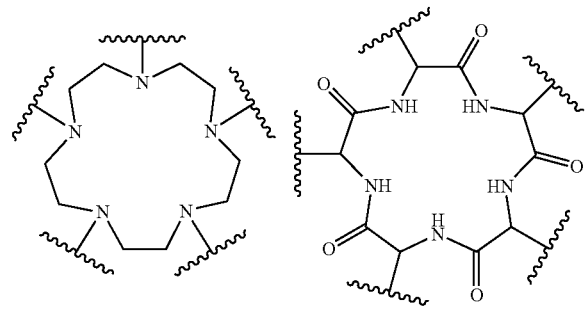
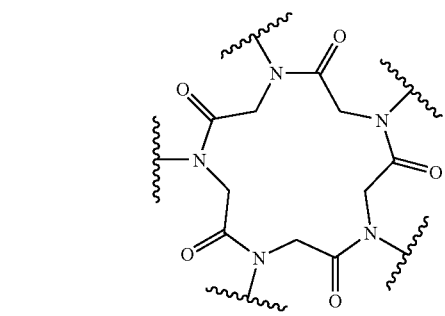
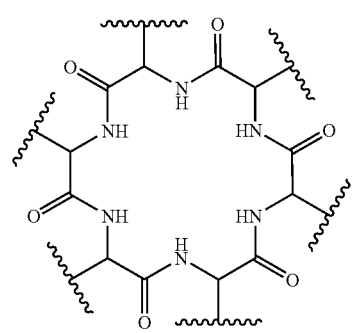
-continued
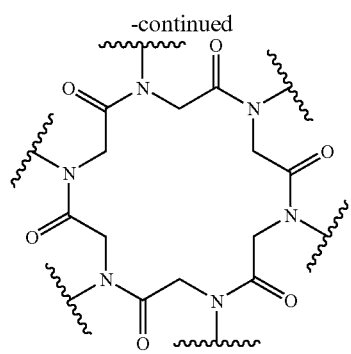
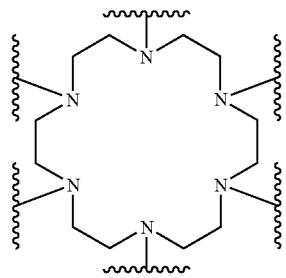
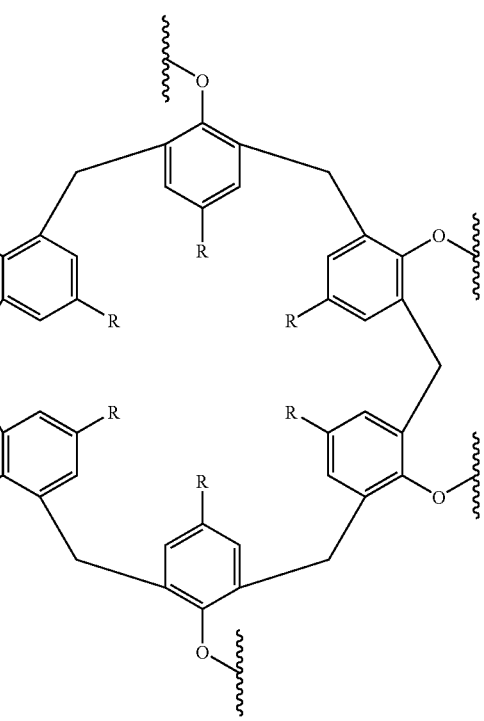
wherein Y is a group of the formula:
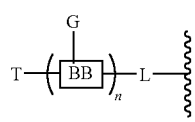
wherein about 2 to about 6 Y are attached C;

wherein Z has the formula:

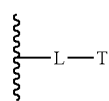

wherein one Z is attached to C or is absent;
wherein each L is separately selected from the group consisting of: an oligopeptide comprising 1 to 12 amino acid residues, an optionally substituted $C_1$-$C_{12}$ alkyl, an optionally substituted $C_2$-$C_{12}$ alkenyl, an optionally substituted $C_2$-$C_{12}$ alkynyl, an optionally substituted $C_{3-12}$ cyclic alkyl, alkenyl, alkynyl, or aromatic moiety, —C(=O)NH—, —C(=O)NHO—, —C(=O)NHNH—, —S(=O)(=O)NR—, —P(=O)(—OR)NR'—, —SS—, —CH$_2$NR—, —CH$_2$NR—, —CH$_2$C(=O)NR—, —C(=O)O—, —C(=S)NR—, —S(=O)(=O)CH$_2$—, —SOCH$_2$—, and —OC(=O)NR—;
wherein each G is separately selected to be a guanidinium group covalently attached to BB and having the formula:

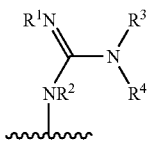

wherein the point of attachment of G to BB is through a nitrogen atom or through $R^2$ or each G is separately selected from the group consisting of:

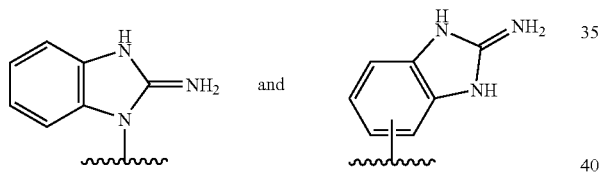

each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;
each $R^1$ is optionally bound to the $R^2$, $R^3$, or $R^4$ on the same guanidinium group to form a heterocyclic ring;
each $R^2$ is optionally bound to the $R^3$ or $R^4$ on the same guanidinium group to form a heterocyclic ring; and
each $R^3$ is optionally bound to the $R^4$ on the same guanidinium group to form a heterocyclic ring;
wherein each BB-G is separately selected from the group consisting of

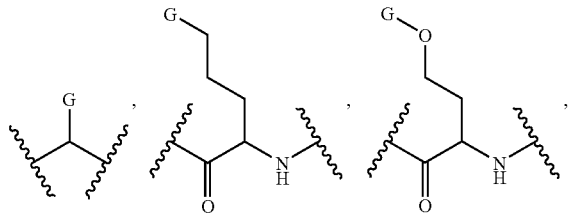

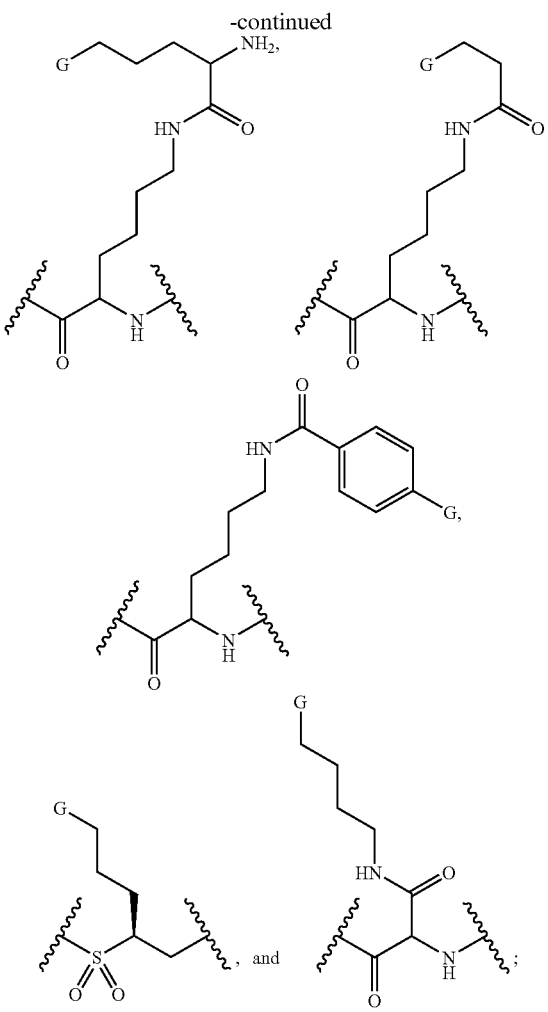

wherein each T is a terminal group separately selected from the group consisting of hydrogen, an amine group, a carboxylic group, a N-terminal peptide or group that forms an N-terminal peptide bond with BB, a C-terminal peptide or group that forms an C-terminal peptide bond with BB, a reporting moiety, a targeting moiety, and a therapeutic moiety or T is absent;
wherein each n is separately selected to be an integer from 1 to 8;
wherein each R and R' are separately selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl;
q is an integer from 0 to 10;
r is an integer from 0 to 3; and
s is an integer from 0 to 1.

Also disclosed herein is a compound that includes a symmetric core moiety and a plurality of side chains covalently attached to the symmetric core moiety, wherein at least two of the side chains comprise at least one guanidinium group.

Also disclosed herein is a method for enhancing transport of a biologically active moiety across a biological membrane, comprising contacting a biological membrane with one of the compounds disclosed above, wherein at least one T comprises a biologically active moiety, whereby the contacting is effective to promote transport of the compound across the biological membrane at a rate that is greater than a transmembrane transport rate of the biologically active moiety in non-conjugated form. In some embodiments, the biological membrane is a eukaryotic cell membrane. In some embodiments, the biological membrane is a prokaryotic cell membrane.

DETAILED DESCRIPTION OF THE PREFERRED EMBODIMENT

Figure 1:
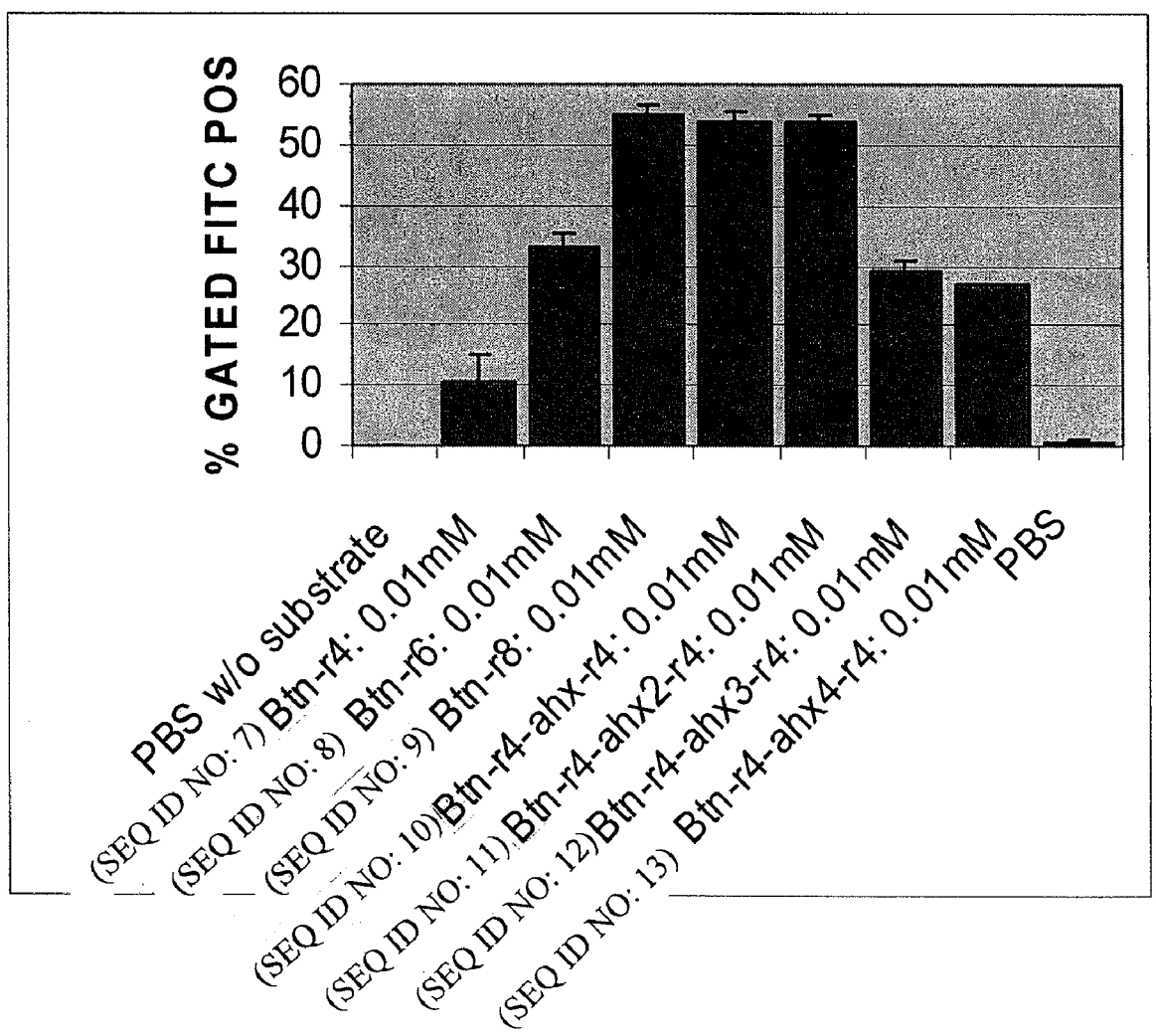
FIG. 1 is a bar graph depicting cellular uptake efficiency of several oligoarginine compounds and novel divalent arginine compounds.

Oligoarginine sequences generated by replacing non-arginine residues with arginine in the HIV Tat 47-57 segment have been demonstrated to be effective at assisting molecules to cross cellular membranes and mammalian skin tissues. Oligoarginine sequences may function through disruption of the cellular membranes rather than specific interaction with cell surface receptors. Evidence supporting this theory has demonstrated that: (1) cellular uptake of oligoarginine can take place at 4° C., where endocytosis processes are inhibited, (2) the cellular uptake efficiency depends on the number of arginine residues in the molecule, and (3) cellular uptake efficiency is not affected by backbone chirality, backbone composition, or the exact position of arginine attachment on the backbone. Cellular uptake efficiency of these molecules appears to not be affected by insertion of other amino acid residues between the arginine residues. The electrostatic interactions between oligoarginines and fatty acid may be responsible for the partition of the highly polar oligoarginines into the lipid phase of the biological membrane. Methylation of guanidinium groups was demonstrated to cause a decrease in the cellular uptake efficiency of oligoarginines due to the fact that less hydrogen bonds can be formed.

In contrast to the theory that oligoarginine molecules operate by cell membrane disruption, specific interaction between oligoarginine and the cell surface receptor heparin may induce endocytosis of the oligoarginine. See Fuchs and Raines, Biochemistry (2004) 43, 2438-2444, which is incorporated herein by reference in its entirety. Oligoarginine has been exclusively observed in the endocytic vesicles of the living cells. In addition, oligoarginine was unable to enter living cells deficient in heparin sulfate.

Competing theories for the mechanism of oligoarginine uptake into cells suggests a complex process that exploits different routes under different conditions. While not being bound by any particular theory, membrane disruption may be dominant at low temperature while specific receptor-ligand interactions followed by endocytosis may become more significant under physiological conditions. Because receptor-ligand interactions may be an important feature in uptake mechanism, it may be advantageous to design arginine based transporter molecules that exploit the positioning of receptors on a cell's surface.

In one embodiment, multivalent arginine transporter molecules are provided to maximize arginine-receptor interactions. Multivalent arginine transporter molecules contain multiple guanidinium functionalities that can bind with multiple guanidinium binding sites on cell surface receptors. The structure of a multivalent arginine transport molecule causes multiple guanidinium functionalities to be brought within close proximity of binding sites once one such functionality binds to a binding site. Thus, the overall entropy is decreased and transport of the multivalent arginine transporter molecule into the cell is enhanced.

In some embodiments, a multivalent arginine transporter molecule is provided having one or more therapeutic moieties attached thereto. Thus, the transporter-therapeutic complex can be readily transported into a cell where the therapeutic moiety can have therapeutic effect. Any therapeutic moiety that can be covalently bound to the multivalent arginine transporter molecules disclosed herein may be used. Non-limiting examples of some therapeutic moieties include: immunosuppressives, antibacterials, antifungals, antivirals, antiproliferatives, hormones, antiinflammatories, vitamins, analgesics, diagnostics and imaging contrast agents. Some specific examples include: conjugated glucocorticoids for treating inflammatory skin diseases, conjugated retinoids for treating acne, skin cancer and psoriasis, conjugated cytotoxic and immunosuppressive drugs for treating cancer and leukemia, conjugated antiinflammatory and antifungal agents, conjugated antihistamines, conjugated anagelsics, conjugated photochemotherapeutic agents, sunscreen, conjugated antibiotics for treating bacteria infections, conjugated anti-neoplastic agents for treating cancers, conjugated antiinflammatory agents, bronchodialators and immunosuppressive drugs for treating pulmonary conditions, conjugated neurotransmitters, and analgesics and CNS drugs that are capable of crossing blood brain barrier.

In some embodiments, the therapeutic moiety is attached to the transporter molecule via a cleavable linker moiety. The cleavable linker moiety may be such that once the transporter-therapeutic complex is transported into a cell, the linker is cleaved, freeing the therapeutic moiety from the complex. Those of skill in the art will recognize many cleavable linkers suitable for this purpose. Non-limiting examples of cleavable linkers include moieties containing di-sulfide functionalities or acid-degradable functionalities such as esters. In some embodiments, a targeting moiety may also be attached to the multivalent arginine transporter molecule. The targeting moiety may be any moiety that preferentially binds to receptors on one or more cell types. Thus, a transporter-targeting-therapeutic complex is provided that preferentially is transported into one or more cell types where the therapeutic moiety can have therapeutic effect. Those of skill in the art will recognize many suitable targeting moieties. Non-limiting examples of some targeting moieties include: small molecules, oligo peptides, oligonucleotides, and macromolecules obtainable from synthetic or natural resources that have specific interactions with molecular targets implicated in the following diseases, including Acute lymphoblastic leukemia, Advanced pancreatic tumor, Affective disorder, AIDS, Allergic rhinitis, Allergy, Alzheimer's, Analgesic, Anesthesia, ANF degradation, Angiogenesis, Anxiety, Arthritis, Asthma, Autoimmune disease, Bacterial infection, Baldness, Blood coagulation, Bone Loss, Brain ischaemia, Breast cancer, Calcium deficiency, Carcinoid syndrome, Cardiac failure, Cardiovascular disease, Chronic myelogenous leukemia, Cognitive dysfunction, Colon cancer, Common cold, Common roundworm, Congestive heart failure, Cystic fibrosis, Dementia, Depression, Diabetes, Diabetic retinopathy, Diarrhea, Drug dependence, Erectile dysfunction, Fever, Fungal infection, Gastric tumor, Glaucoma, Gout, Heart disease, Heart failure, Helminth infection, Hepatitis C, Herpes, High blood glucose level, High blood sugar level, High cholesterol, Hirsutism, Hormone-dependent tumors, Human African trypanosomiasis, Hypertension, Hyperthyroidism, Hypocalcaemia, Immune response, Immunodeficiency, Inflammation, Influenza A and B, Insomnia, Irritable bowel syndrome, Kidney failure, Leukemia, Liposarcoma, Liver, Local anesthetic, Lung cancer, Lupus, Malaria, Malignant pain, Melanoma, Metastasis, Migraine, Morning sickness, Motion sickness, Motor disorder, Movement disorder, Nasal congestion, Neurodegeneration, Neuropathic, Obesity, Obstructive pulmonary disease, Ocular hypertension/glaucoma, Osteoporosis, Ovarian, Pain, Parkinson's, Peptic ulcer, Phaeochromocytoma, Platelet adhesion, Platelet disease, Posterior pituitary disorder, Post-surgical pain, Prostate adenocarcinoma, Prostate tumor, Prostatic hyperplasia, Psychiatric illness, Psychomotor, Reproduction diseases, Respiration diseases, Rheumatoid, Riboflavin deficiency, Schizophrenia, Seizure, Smoking addiction, Solid tumor, Thiamine deficiency, Tuberculosis, Urinary tract infection, Urticaria, Uterus contraction, Vascular disease, Viral infection, Visceral, Vitamin A deficiency, Vitamin B12 deficiency, Vitamin B6 deficiency, Vitamin C deficiency, Vitamin D deficiency, Vomiting, and Zollinger-Ellison syndrome.

In one embodiment, the multivalent arginine transporter molecules for use as described herein have the structure:

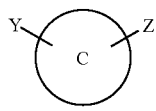

C represents a core moiety comprising an organic fragment. The core moiety C provides a molecular scaffold around which various arginine containing side chains Y may be attached. The attachment of multiple side chains Y yield a multivalent structure that provide entropy benefits when the molecule binds to receptors on a cell's surface. The multiple Y side chains on a particular core moiety may either be the same or different. Each Y side chain may have any number of guanidinium functional groups. Furthermore, each Y side chain may have a terminal group that can include a therapeutic or targeting moiety. In addition, a side chain Z having a biologically active moiety, such as a therapeutic moiety or a targeting moiety, may optionally be attached to the core moiety C. In some embodiments, the core moiety has a molecular weight less than about 50,000. In some embodiments, the core moiety has a molecular weight less than about 10,000. In some embodiments, the core moiety has a molecular weight less than about 5,000.

In some embodiments, the core moiety C is a symmetric molecular fragment. Thus, the side chains Y and Z can be covalently attached to C in a symmetric configuration around C. Non-limiting examples of suitable symmetric core moieties C include the following structures:

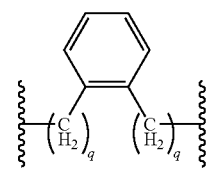
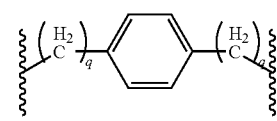
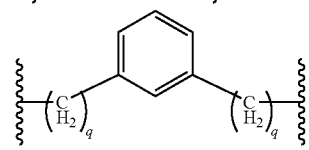
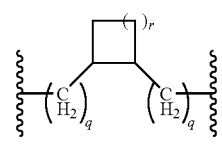

-continued

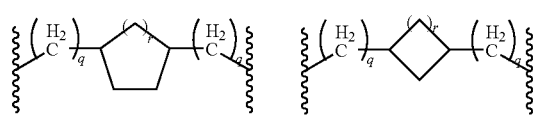

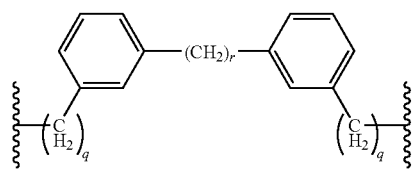

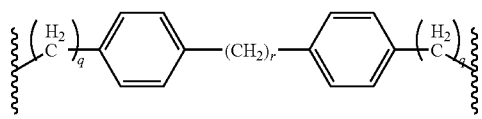

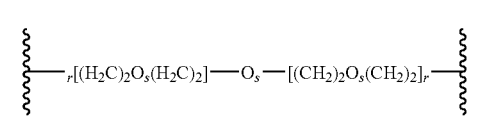

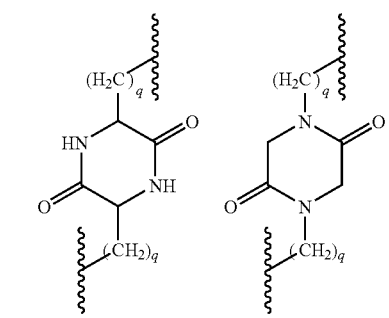

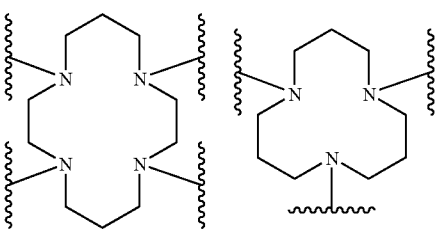

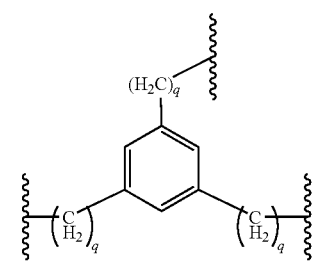

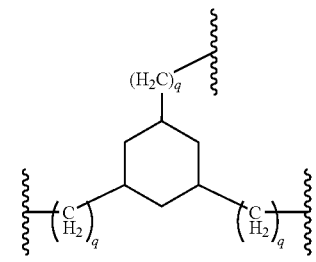

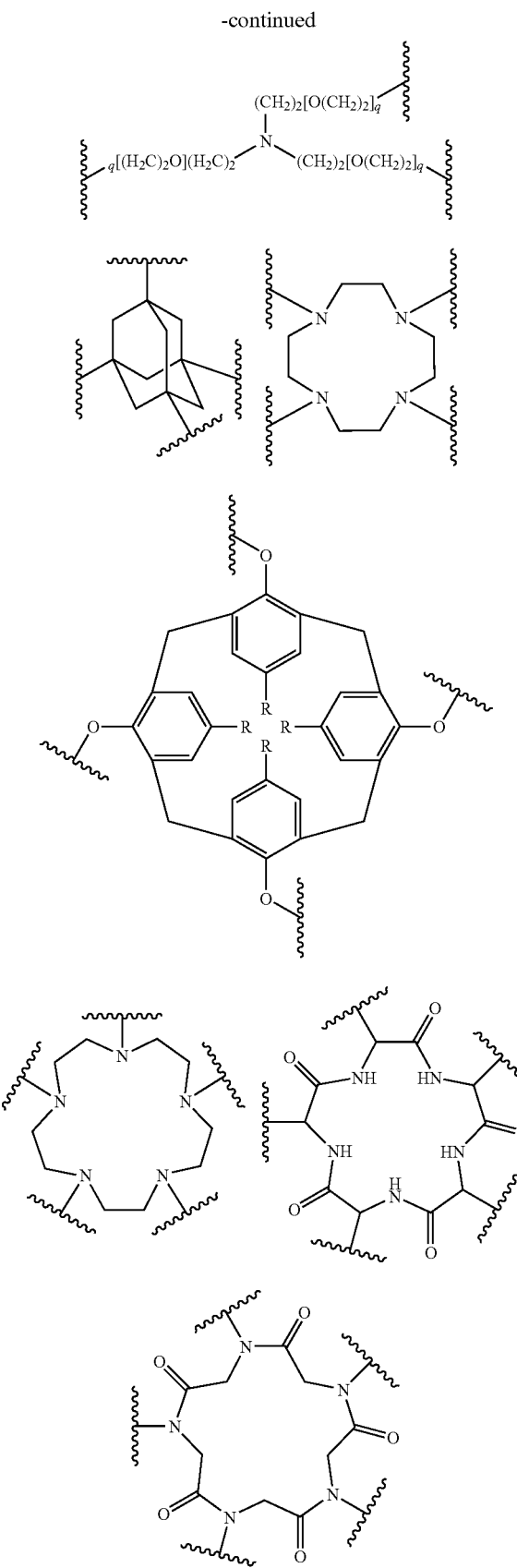
where wavy lines indicate covalent attachment points, q is an integer from 0 to 10, r is an integer from 0 to 3, s is an integer from 0 to 1, and R is selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl. Those of skill in the art will recognize other suitable symmetric or non-symmetric core moieties for use as described herein.

In some embodiments, about 2 to about 20 Y groups are attached to C. Each attached Y group may be the same or different from other attached Y groups. In some embodiment, each Y group has the formula:

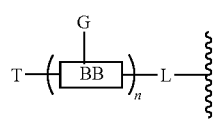

L is a linker moiety comprising a molecular fragment that links the rest of each side chain Y to core moiety C. The linker moiety L in each separate Y group may be the same or different from other linker moieties L in other Y or Z groups. As discussed above, linker moiety L may optionally be a cleavable linker designed to cleave a Y group from the transporter molecule under certain conditions. In some embodiments, L is a molecular fragment having a molecular weight less than about 5000. In some embodiments, L is a molecular fragment having a molecular weight less than bout 1000. In some embodiments, L is a molecular fragment having a molecular weight less than about 500.

BB is a backbone moiety comprising an organic fragment that provides a scaffold upon which guanidinium moieties G may be attached. Multiple backbone moieties BB may be linked together to from a linear chain of backbone moieties within each Y group. In general, about 1 to about 8 backbone moieties may be included in each Y group (e.g., n is an integer from about 1 to about 8). When multiple backbone moieties BB are in a given Y group, each BB group in the Y group may be the same or different from other BB groups in the same Y group. Furthermore, each BB group in a Y group may be the same or different from other BB groups located in other Y groups. In one simple example, BB-G is an arginine residue. Thus, one particular Y group may include an oligoarginine chain. In one embodiment, BB is an organic fragment having a molecular weight less than about 10,000. In one embodiment, BB is an organic fragment having a molecular weight less than about 5,000. In one embodiment, BB is an organic fragment having a molecular weight less than about 1,000.

Some non-limiting examples of backbone moieties BB with attached guanidinium groups G include:

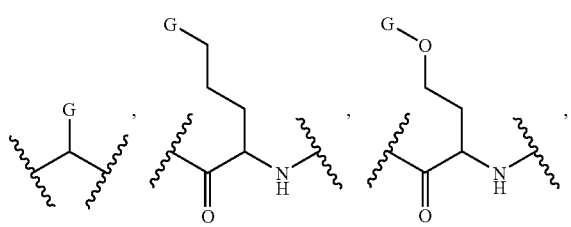

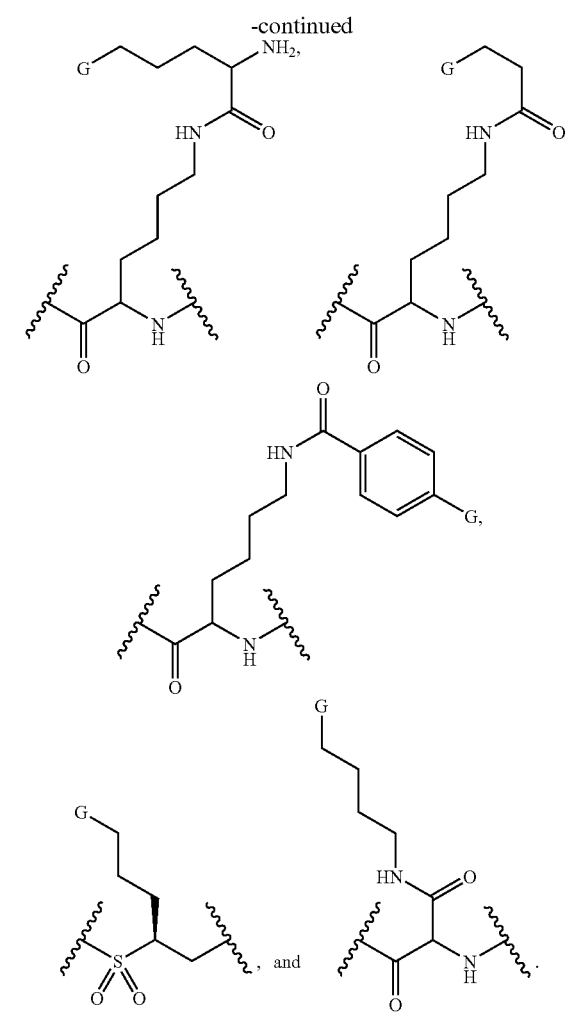

G represents a guanidinium moiety and may have the structure:

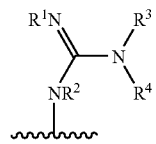

where the point of attachment of G to BB is through the nitrogen atom or through $R^2$ or, alternatively, each G may be selected from the group consisting of:

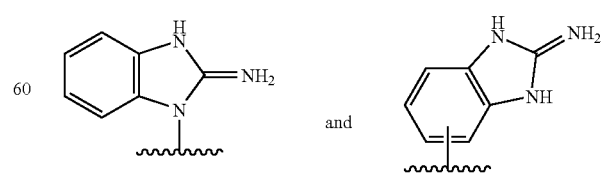

Each $R^1$, $R^2$, $R^3$, and $R^4$ may be separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and an N protecting group such as pentamethylchroman-6-sulfonyl. The wavy line indicates where guanidinium moiety G attaches to a backbone moiety BB. $R^1$, $R^2$, $R^3$, and $R^4$ on each guanidinium moiety G may be the same or different from $R^1$, $R^2$, $R^3$, and $R^4$ groups on other guanidinium moieties G. In some embodiments, $R^1$ may be optionally bound to a $R^2$, $R^3$, or $R^4$ group on the same guanidinium group to form a heterocyclic ring within the guanidinium group. Similarly, in some embodiments, $R^2$ may be optionally bound to a $R^3$ or $R^4$ group on the same guanidinium group to form a heterocyclic ring or $R^3$ may be optionally bound to the $R^4$ on the same guanidinium group to form a heterocyclic ring.

Some non-limiting examples of G include:

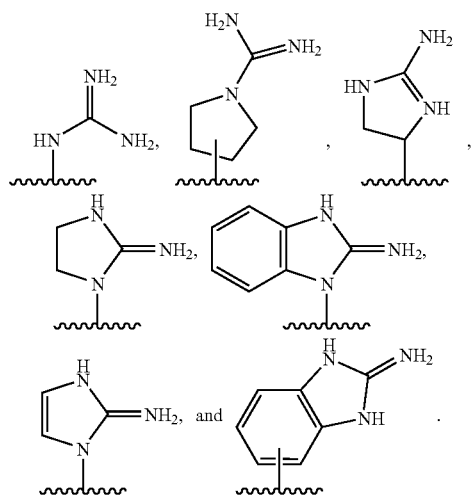

T represents a terminal group attached to the end of each Y group. Terminal group T may serve the function of merely terminating the backbone moiety chain or may also include therapeutic, targeting, or reporting moieties. When a terminal group T includes a therapeutic moiety, the moiety may be linked to the rest of the Y group through a cleavable linker such as described above. Each T group on a Y group may be the same or different from T groups on other Y or Z groups. In some embodiments, each terminal group T may be separately selected from the group consisting of hydrogen, an amine group, a carboxylic group, a N-terminal peptide or group that forms an N-terminal peptide bond with BB, a C-terminal peptide or group that forms a C-terminal peptide bond with BB, a reporting moiety, a therapeutic moiety, and a targeting moiety. Alternatively, a T group may be absent if the terminal BB group does not require a terminating group, such as when a guanidinium moiety G terminates the backbone chain.

In some embodiments, a Z side chain may also be optionally attached to core moiety C. In one embodiment side chain Z has the formula:

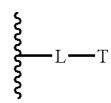

The wavy line indicates where side chain Z attaches to core moiety C. L in the formula for Z represents a linker moiety as described above. The linker moiety L may be the same or different from linker moieties L located on Y groups in the same molecule. T represents a terminal group as described above. The terminal group T may be the same or different from terminal groups T located on Y groups in the same molecule. Side chain Z provides a means for attaching a therapeutic, reporting, or targeting moiety to the transporter molecule through a linker that doesn't require guanidinium groups.

Some non-limiting examples of compounds as defined above include:

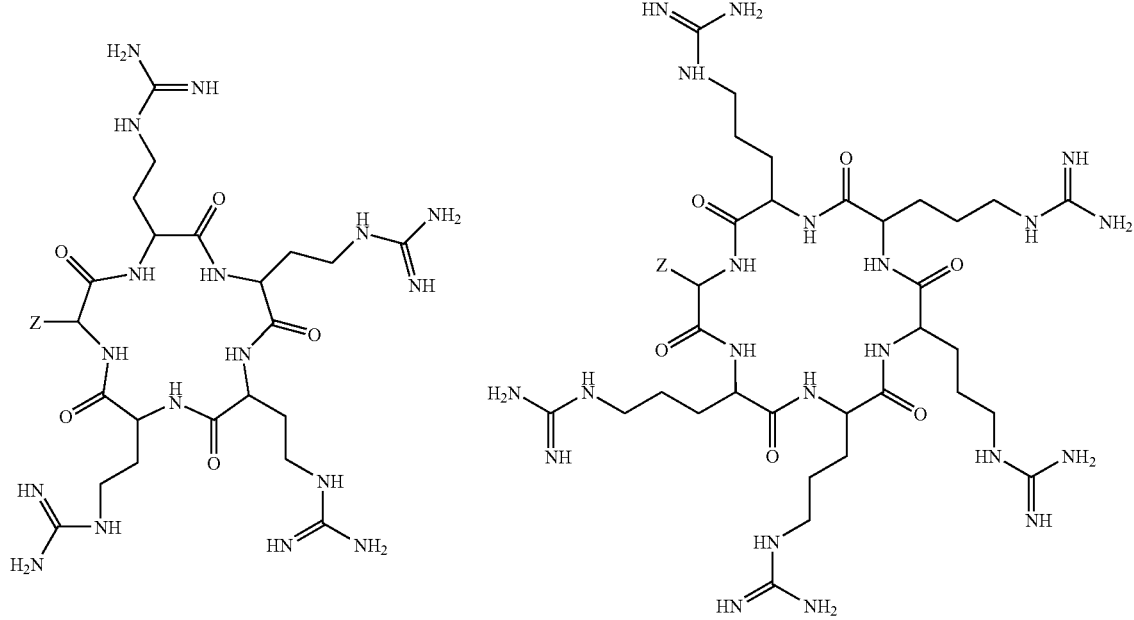

-continued

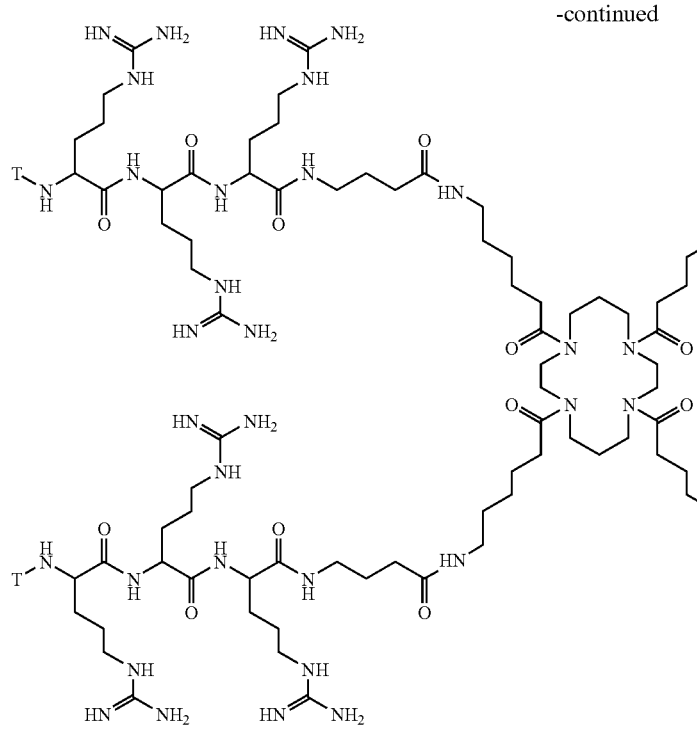
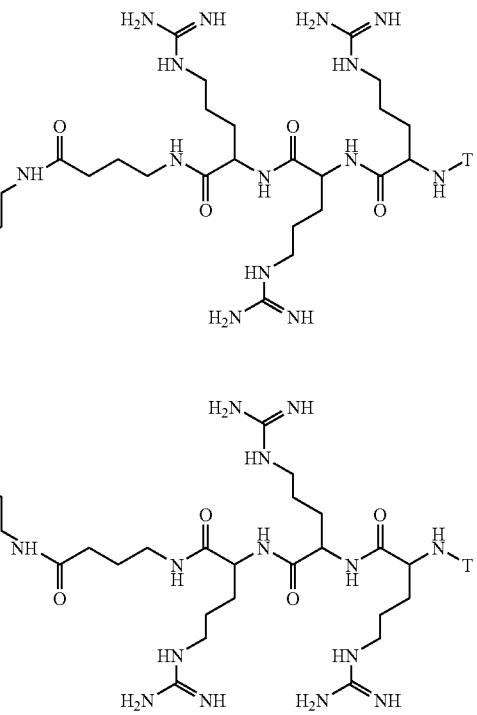

In some embodiments, the multivalent arginine transport molecules described above are cyclic alternative D,L-peptoids, which are cyclic polypeptides where the amino acids in the amino acid chain alternate between the D configuration and the L configuration. This class of compounds has the unique structural feature that all of the side chains extend fully outward with the backbone amide C═O and N—H pointing alternatively up and down along the axis of the cyclic plane. Thus, in molecules with side chains containing guanidinium moieties, the guanidinium moieties will all be pointing outward and thus available for interaction with surface receptors or membrane lipids. In contrast, linear oligoarginine contains some guanidinium groups that point away from a cell surface when the oligoarginine interacts with the surface because of the helical nature of the peptide. These guanidinium groups will not be able to interact with surface receptors or membrane lipids.

In some embodiments, the cyclic peptoids have the structure:

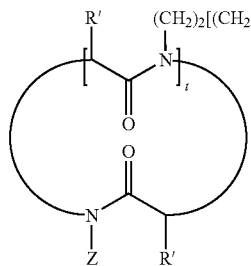

Each unit t may be repeated and are bound together so as to form a ring. The subscript t may be an integer from about 1 to about 20. G and Z are as defined above. Each G group in each unit t may be the same or different from other G groups in other unit t's. The subscript u may be an integer from 0 to 1 and the subscript v may be an integer from about 0 to about 10. Each R' may be separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; amino; aminocarbonyl; aminocarboyloxy; nitro; azido; phenyl; hydroxy; alkylthio; arylthio; oxysulfonyl; carboxy; cyano; and halogenated alkyl including polyhalogenated alkyl. Each R' may be the same or different from other R's.

Some non-limiting examples of cyclic peptoids for use as described herein include:

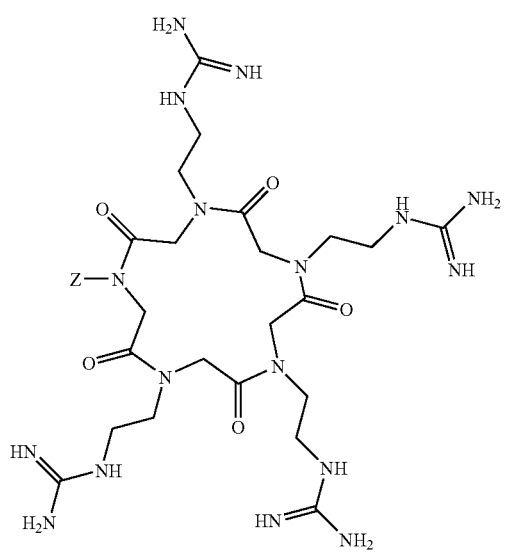

-continued

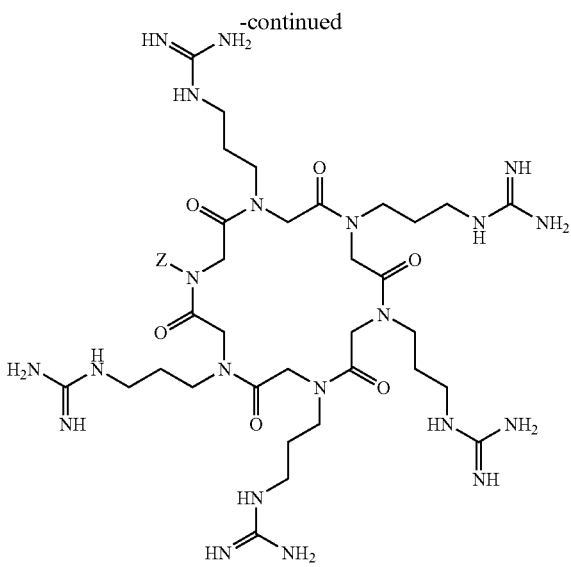

Where the compounds disclosed herein have at least one chiral center, they may exist as a racemate or as enantiomers. It should be noted that all such isomers and mixtures thereof are included in the scope of the present invention. Furthermore, some of the crystalline forms for the compounds of disclosed herein may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

In some embodiments, the compounds disclosed herein may be provided in a pharmaceutically acceptable salt. The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein can be used alone, in combination with other compounds disclosed herein, or in combination with one or more other agents that are therapeutically active.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcoalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

Unless otherwise indicated, the substituent "R" appearing by itself and without a number designation refers to a substituent selected from the group consisting of alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(=O)O— group, where R is as defined herein.

A "C-carboxy" group refers to a —C(=O)OR groups where R is as defined herein.

An "acetyl" group refers to a —C(=O)$CH_3$, group.

A "trihalomethanesulfonyl" group refers to a $X_3CS$(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a $X_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—$NR_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include $CH_3$C(=O)$CH_2$—, $CH_3$C(=O)$CH_2CH_2$—, $CH_3CH_2$C(=O)$CH_2CH_2$—, $CH_3$C(=O)$CH_2CH_2CH_2$—, and the like.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "heterocyclyl" is intended to mean three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzofused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro- 1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, the term "guanidinium group" refers to a moiety having the formula:

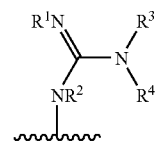

where $R^1$, $R^2$, $R^3$, and $R^4$ are as described above and the wavy line represent the point of attachment of the group to the rest of a molecule.

Methods of Preparation

The compounds disclosed herein may be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

Core moieties for use in the compounds described herein may be synthesized or obtained from commercially available sources. In some embodiments, side chains may be attached to the core moiety via amine groups present in the core moiety. In such compounds, a linker moiety may be attached to the core moiety by reaction of linker groups containing a carboxylic functionality with the amine functionalities in the core moiety to form peptide bonds between the linker moieties and the core moiety.

Backbone moieties with attached guanidinium groups may be synthesized using solid-phase chain grown reactions. For example, an Fmoc-GABA-OH group may be attached to a resin, such as HMPB-AM, to form an anchor for chain grown. BB-G moieties may then be polymerized on the anchor to form a chain of desired length. In some embodiments, polymerization of BB-G moieties may be through the formation of an oligopeptide chain. In one simple example, the BB-G chain may comprise oligoarginine, which can be generated by forming an arginine peptide chain with the guanidinium groups protected by a protecting group, such as Pmc, which can be subsequently removed. Finally, a terminal moiety, such as described above, may be attached to the end of the chain, such as through a peptide bond. After the terminal moiety is attached, the chain may be cleaved from the resin such as through treatment with TFA, forming a GABA terminated chain. The carboxylic group in the GABA moiety may be reacted with amine groups in the linker moieties discussed above to form a peptide bond between the linker moiety and the backbone moiety, thus forming the multivalent compounds described herein.

Although many of the linkages in the synthetic method described above involve formation of peptide bonds, those of skill in the art will recognize other functional groups that could be used to form linkages between the components of the molecule, such as by forming ester bonds between the linker moiety and the core moiety.

In some embodiments, cyclic peptoid compounds described herein may be synthesized by the following scheme:

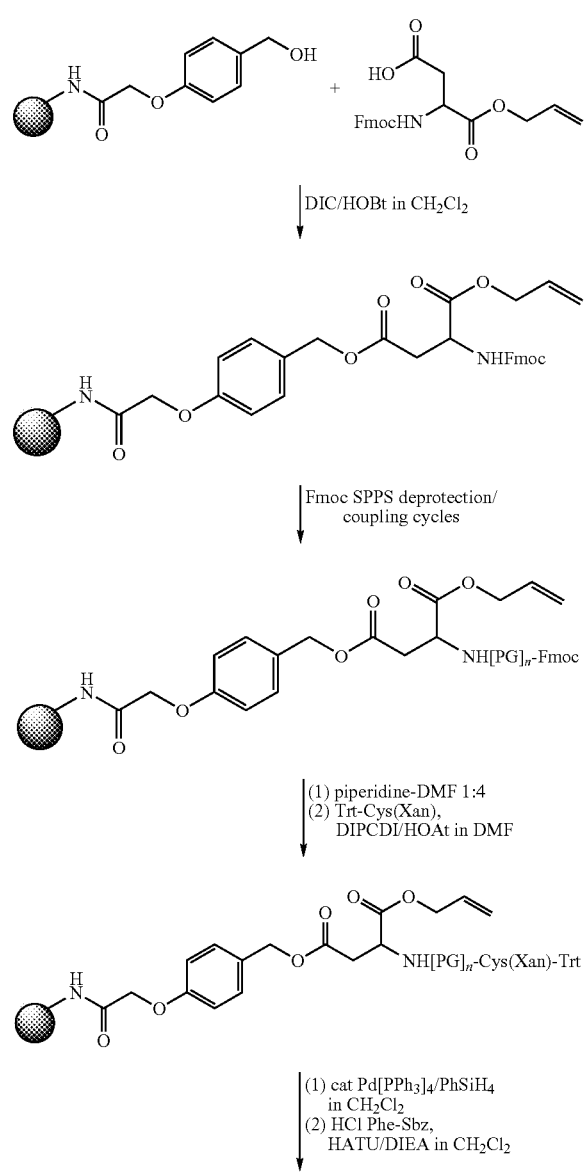

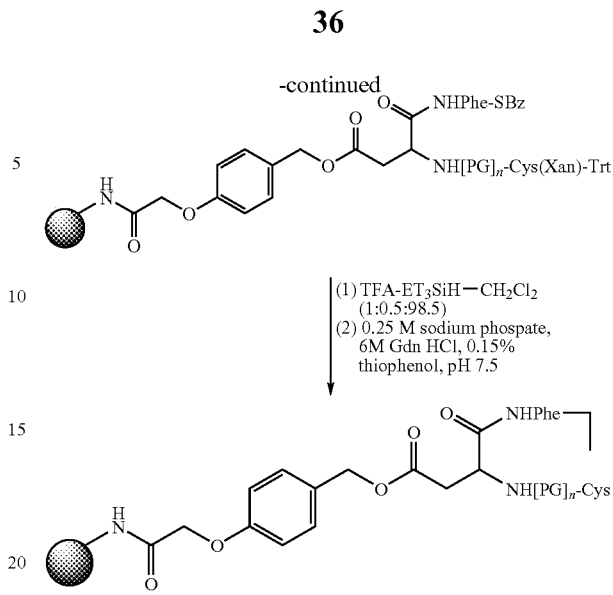

First, a resin with attached anchor group is formed. Next, a peptide chain containing the desired guanidinium group and optionally a desired terminal group is formed by sequential formation of peptide bonds, such as in the chain growth method described above. PG in the above scheme represents an amino acid residue containing at least one guanidinium functionality. In one simple embodiment, the amino acid residue is arginine. Finally, after a series of preparative steps, a cyclic compound is formed. The resulting cyclic peptoid may be cleaved from the resin using a suitable cleavage reaction. Terminal groups, such as therapeutic moieties, may be incorporated into the cyclic peptoid by either including the group in one or more of the amino acid residues PG or in one of the steps after peptide polymerization.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

Methods of Use

In some embodiments, the multivalent transporter molecules described above may be used to enhance transport of a drug across a cell membrane. In one embodiment, enhancing transport of a drug across a cell membrane comprises linking a therapeutic moiety to the multivalent transporter molecule. The therapeutic moiety may be any suitable radical of a therapeutically effective drug. In some embodiments, the therapeutic moiety is linked to the transporter molecule via a cleavable linker such that when the molecule is within a cell, the therapeutic moiety is cleaved, generating the drug molecule. In some embodiments, a targeting moiety is also attached to the transporter molecule. The targeting moiety may be a moiety that preferentially binds to receptors on one or more cell types. Thus, the transporter molecule will have increased affinity to particular cell types, and thus increased transport across the membrane of those cell types. In this way, a drug can be effectively delivered specifically to the interior of cells where the drug will have its most beneficial effect.

In some embodiments, a method is provided for converting a drug to a form that is more bioavailable. The method may comprise linking the drug to a transporter molecule as described herein. The transporter molecule will exhibit enhanced transport across cellular membranes and thus the attached drug will be more bioavailable than when delivered alone.

In some embodiments, the transporter molecules described herein may similarly be used to enhance transport of a drug across epithelial tissue, such as across skin.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Ophthalmologica,* 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the therapeutic moiety incorporated, the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

Synthesis of 1,4,8,11-Tetrakis(ε-aminohexylcarbonyl)-1,4,8,11-tetraazacyclotetradecane (3) (A Tetravalent Core with Peptide Linkers)

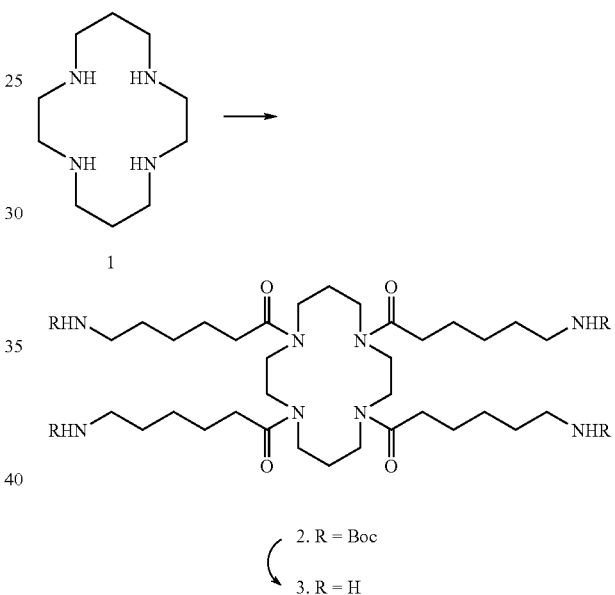

A solution of 6-(BOC-amino)caproic acid (2.38 g, 10.3 mmole) in $CH_3CN$ (20 ml) was treated with carbonyldiimidazole (CDI) (1.65 g, 10.1 mmole) at room temperature for 30 min. The solution was then added dropwise to a suspension of 1,4,8,11-tetraazacyclotetradecane (compound 1) (0.1720 g, 0.85 mmole) in 1000 ml of $CH_3CN$ and 1 ml of DIPEA. The reaction was stirred at room temperature for 7 days. The solvent was removed by rotary evaporation. To the residue was added 300 ml of ethyl acetate. The organic layer was washed with 5% citric acid (2×300 ml), 10% $NaHCO_3$ (300 ml) and water (300 ml), and was dried over anhydrous $Na_2SO_4$. After removing the drying agent by filtration, the solvent was removed by rotary evaporation. The residue was treated with 6 ml of $TFA:CH_2Cl_2$ (1:1) and was shaken for 3 hours. After the solvent was removed by rotary evaporation, the residue was dissolved in water and was neutralized to pH 2.0 with $NaHCO_3$ solution. The product was purified by reverse-phase HPLC chromatography in semi-preparative column with $CH_3CN$ and 0.1% aqueous TFA solution as mobile phases. The product (compound 3) was dried by lyophilization to give 0.54 g of product (80% yield).

Example 2

Synthesis of N-Btn-Arg(Pmc)-Arg(Pmc)-Arg(Pmc)-GABA-OH (4) (SEQ ID NO: 1) (An Oligoarginine Side Chain)

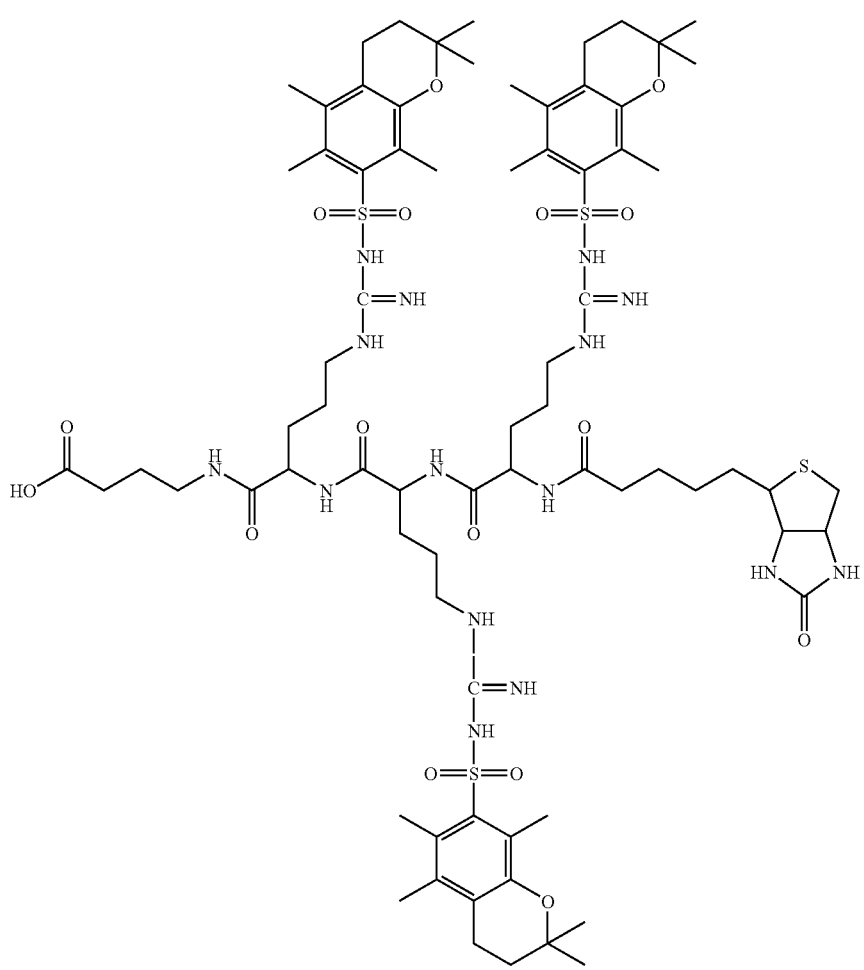

I. Attaching Fmoc-GABA-OH on HMPB-AM Resin

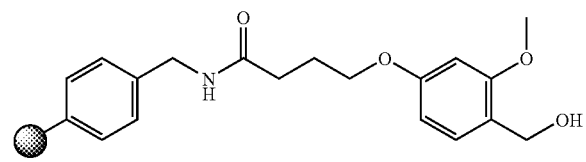

HMPB-AM resin (1 g, Novabiochem, 0.54 mmole/g) was placed in a clean and dry flask and was covered by DMF to allow to swell. In another flask, Fmoc-GABA-OH (10 eq. relative to resin loading) was dissolved in dry DCM, and a small amount of DMF was added to guarantee complete dissolution. To this solution was added diisopropylcarbodiimide (5 eq. relative to resin loading). The mixture was stirred for 20 min at 0° C., and the solvent was removed by rotary evaporation. The residue was dissolved in a minimum amount of DMF and was added to the previously described HMPB-AM resin/DMF suspension. To the suspension was added DMAP (0.1 eq. relative to resin loading). The flask was shaken for 1 hr. The resin was thoroughly washed with DMF, DCM and methanol.

II. Extension of Oligoarginine

Synthesis of oligoarginine (n=3) was carried out on the Fmoc-GABA-HMPB-AM resin. Fmoc removal was achieved with piperidine-DMF (1:4, 5 min). 4 eq. of Fmoc-Arg(Pmc)-OH, 4 eq. of HBTU, 4 eq. of HOBt, and 8 eq. of DIPEA was dissolved in DMF to activate for 10 min before mixing with the resin. The coupling was carried out under bubbling nitrogen gas for 1 hr. Biotin was added as a model terminal group. Biotinylation was carried out on the resin following the same coupling procedure.

III. Cleavage

After the chain assembly was complete, the resin was thoroughly washed with DMF and DCM. The resin was treated 10 times with 10 ml of 1% TFA in DCM. Each treatment lasted for 10 min under regular stirring. The cleavage mixture was then drained to a container containing 2 ml of 10% pyridine in methanol. The filtrates were combined and the solvent was removed by rotary evaporation. While being cooled in an ice bath, 40 ml of water was added to the residue. The resultant precipitate was collected by filtration and was dried via lyophilization.

Example 3

Synthesis of a Tetravalent Transporter Molecule

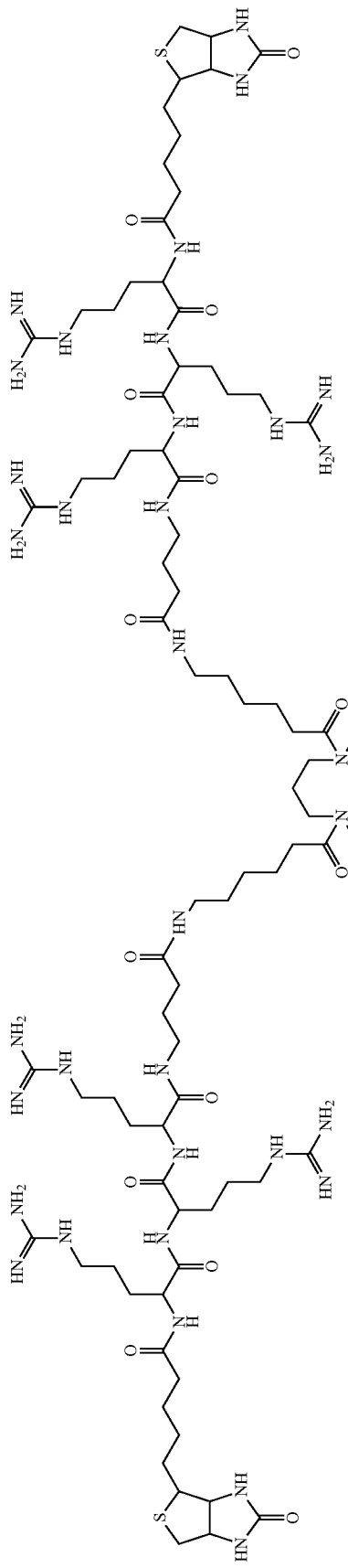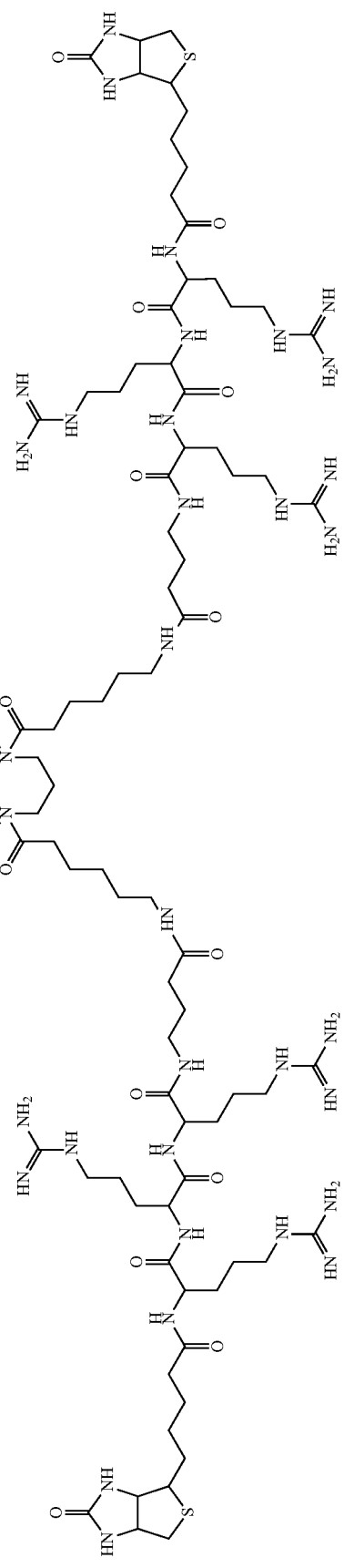

N-Btn-Arg(Pmc)-Arg(Pmc)-Arg(Pmc)-GABA-OH (SEQ ID NO: 1) (compound 4 from Example 2) (150 mg, 0.094 mmole), HBTU (35 mg, 0.094 mmole) and HOBt (12 mg, 0.094 mmole) was dissolved in 1 ml of DCM. 35 mL of DIPEA (0.2 mmole) was added to the mixture. A solution of 10 mg of 1,4,8,11-Tetrakis(ε-aminohexylcarbonyl)-1,4,8,11-tetraazacyclotetradecane (compound 3 from Example 1) in 0.5 ml of DCM was added dropwise to the above solution. The mixture was stirred at room temperature overnight. The solvent was removed by rotary evaporation, and to the residue was added 2 ml of TFA:DCM (1:1). The solution was further stirred at room temperature for 2 hrs. The solvent was again removed by rotary evaporation at the end. The product was purified by reverse phase HPLC using 0.1% aqueous TFA and $CH_3CN$ as mobile phase. 24 mg of product was obtained after the collection was lyophilized.

Example 4

Synthesis of S-(9H-Xanthen-9-yl)cysteine

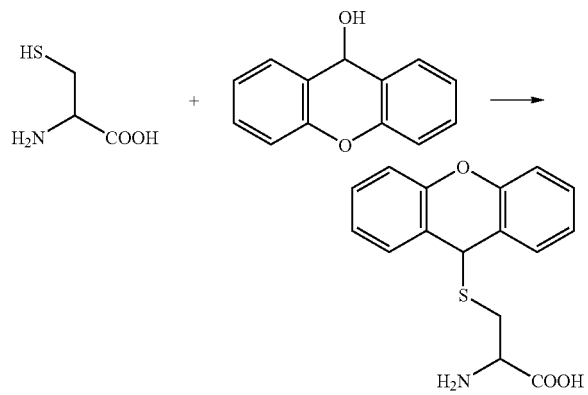

A sample of 0.61 g of cysteine (5 mmole) was suspended in 100 ml of 1,2-dimethoxyethane and 2 ml of TFA. The suspension was stirred under nitrogen gas at room temperature until the solution became clear. To this clear solution was added 1 g of 9H-xanthen-9-ol (5.1 mmole) in one portion. The reaction mixture was stirred at room temperature for 30 minutes and was then neutralized to pH 7 by the addition of a saturated aqueous $Na_2CO_3$ solution. The mixture was then concentrated by rotary evaporation. The residue was diluted with 50 ml of water. The aqueous solution was treated with 10% aqueous citric acid solution to adjust the pH to 6. The mixture was stirred at room temperature for 1 hr. The resultant white solid was collected by filtration and was washed with 3×10 ml of water and 3×10 ml of ethyl acetate. The product was dried to yield 1.30 g of product.

Example 5

Synthesis of $N^\alpha$-Trityl-S-(9H-xanthen-9-yl)-L-cysteine

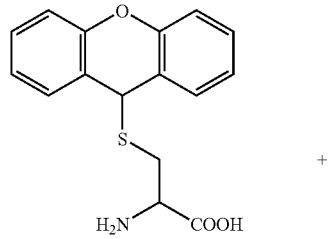

-continued

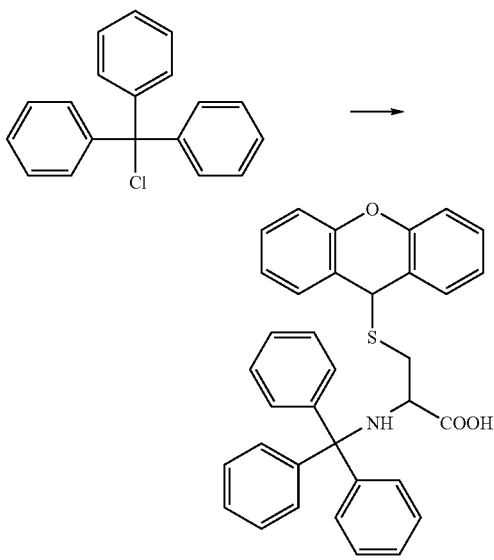

A sample of 1.0 g of S-(9H-Xanthen-9-yl)cysteine (3.3 mmole) from Example 4 was dissolved in 10 ml of chloroform. To the solution was added 1.5 ml of water and 1.5 ml of diethylamine. The mixture was cooled to 4° C. by an ice bath and 0.98 g of trityl chloride (3.5 mmole) was added in portions over a period of 30 min. After 2 h of stirring at room temperature. The reaction mixture was separated. The organic phase was washed twice with 4% diethylamine aqueous solution. The organic layer was dried over $Na_2SO_4$. The drying reagent was removed by filtration and the filtrate was condensed to dryness by rotary evaporation. The residue was refluxed in 10 ml of a 1:30 mixture of diethyl amine/ethyl alcohol. The resultant diethyl ammonium salt was partitioned between 10 ml of ethyl acetate and 7 ml of 5% aqueous $KHSO_4$ and 7 ml of water. The ethyl acetate layer was separated and was dried over $MgSO_4$ and was concentrated to get 1.4 g of product.

Example 6

Synthesis of L-Phenylalanine S-Benzyl Ester

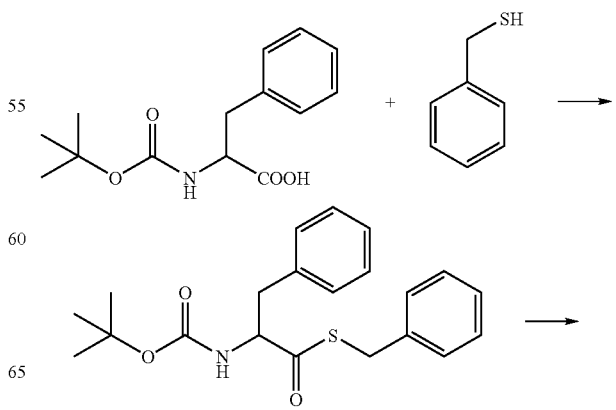

-continued

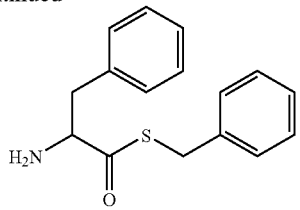

A sample of 1.78 g of Boc-Phe-OH (8.0 mmole) was dissolved in 50 ml of dichloromethane. The solution was cooled to 0° C. by an ice bath. To the solution was added 1.23 g of HOBt (8 mmole), 1.65 g of dicyclohexylcarbodiimide (8 mmole) and 2.74 ml of diisopropylethylamine (16 mmole). After 10 minutes of stirring, 0.94 ml of benzylmercaptan (8 mmole) was added. The resultant mixture was stirred at 0° C. for 2 h and was then allowed to rise to room temperature and the stirring lasted for overnight.

The reaction mixture was washed with 2×150 ml of 1N aqueous HCl, 2×150 ml of 10% aqueous NaHCO$_3$ and 2×150 ml of water. The organic layer was dried over Na$_2$SO$_4$ and was concentrated by rotary evaporation. The residue oil was taken up in 4N HCl on dioxane and was stirred for 90 min to remove the Boc protecting group. The mixture was concentrated to give 1.96 g of product.

Example 7

Synthesis of Fmoc-Asp(HMPA-PEGA)-OAllyl

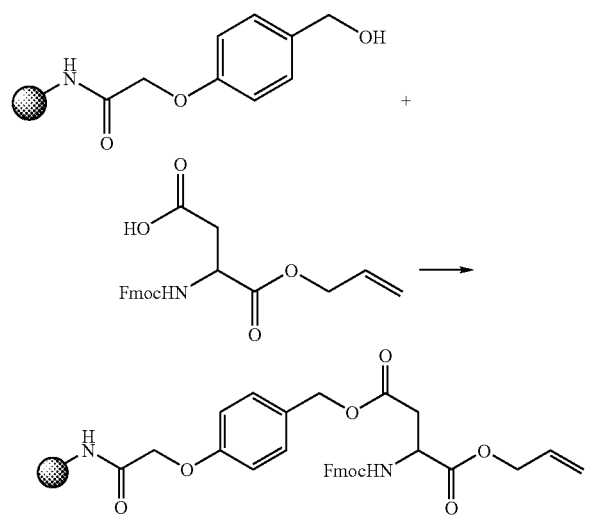

0.3 g of HMPA-PEGA resin (0.4 mmole/g) was washed with DMF (3×1 min) and DCM (3×1 min). 2 eq. of Fmoc-Asp-OAllyl and 2 eq. of HOBt was dissolved in 5 ml of DCM. The mixture was added to the resin. A nitrogen gas was bubbled through the suspension. 2 eq. of DIC and 0.67 eq. of DMAP was added in one portion. The coupling continued for 90 min. The resin was thoroughly washed with DCM and was dried under vacuum.

Example 8

Synthesis of H-Arg(Pmc)-Arg(Pmc)-Arg(Pmc)-Arg(Pmc)-Arg(Pmc)-Arg(Pmc)-Arg(Pmc)-Asp(HMPA-PEGA)-OAllyl (SEQ ID NO: 2)

The Fmoc protecting group on the compound formed in Example 7 was removed by 20% piperidine-DMF solution. 4 eq. of Pmc protected Arg monomer was preactivated by treatment of 4 eq. of HBTU and 4 eq. of HOBt in 2 ml of DMF. The activated monomer was mixed with the resin and 8 eq. of DIPEA was added. The coupling of each Arg monomer lasted for 1 h.

Example 9

Synthesis of Trt-Cys(Xan)-Arg(Pmc)-Arg(Pmc)-Arg(Pmc)-Arg(Pmc)-Arg(Pmc)-Arg(Pmc)-Arg(Pmc)-Asp(HMPA-PEGA)-OAllyl (SEQ ID NO:3)

To the product described in Example 8 was added a DMF solution of 4 eq. of Trt-Cys(Xan)-OH (from Example 5), 4 eq. of HOBt, and 4 eq. of DIC. The mixture was preactivated for 5 min and the concentration for each component was 0.2 M. The coupling reaction lasted for 1 h with a gas of nitrogen bubbling through the suspension.

Example 10

Synthesis of Trt-Cys(Xan)-Arg(Pmc)-Arg(Pmc)-Arg(Pmc)-Arg(Pmc)-Arg(Pmc)-Arg(Pmc)-Arg(Pmc)-Asp(HMPA-PEGA)-OH (SEQ ID NO: 4)

The product of Example 9 was washed with 5×0.5 min of DCM. A solution of 1.6 ml of PhSiH$_3$ in 5 ml of DCM was added and the resin was stirred for 1 min. A solution of 5.4 mg of Pd(PPh$_3$)$_4$ in 3 ml of DCM was added. A nitrogen gas was bubbled through, and the solution was drained after 20 min. The resin was thoroughly washed with 3×1 min of DCM. This deprotection step was repeated once. The removal of the allyl protecting group was confirmed by MALDI mass spectrum of a small cleaved sample.

Example 11

Synthesis of Trt-Cys(Xan)-Arg(Pmc)-Arg(Pmc)-Arg(Pmc)-Arg(Pmc)-Arg(Pmc)-Arg(Pmc)-Arg(Pmc)-Asp(HMPA-PEGA)-Phe-SBz (SEQ ID NO: 5)

To the product of Example 11 was added a solution of 1.2 g of L-Phenylalanine S-Benzyl Ester (Example 6) in 5 ml of DCM and 1.6 ml of DIPEA. The coupling reaction was initiated by adding 870 mg of HATU. The resin was stirred for 30 min at room temperature. The resin was then washed with 5×0.5 ml of DMF and 5×0.5 ml of DCM. A small scale cleavage was carried out to confirm the attachment of this amino acid monomer.

Example 12

Synthesis of cyclo(Cys-Arg-Arg-Arg-Arg-Arg-Arg-Arg-Asp-Phe) (SEQ ID NO: 6)

The product of Example 11 was washed with 3×1 min of DCM. The selective removal of Trt protecting group and the subsequent cyclization was carried out by treating the resin with a mixture of DCM/TES/TFA (89.5%/0.5%/10%). Afterward, the resin was treated with pH 7.5 0.25 M sodium phosphate, 6 M of guanidine chloride and 0.1% of PhSH. The suspension was shaken for overnight. The solution was then drained and the peptide was cleaved off the resin by TFA.

Example 13

FACS Analysis

Hela 705 cells were seeded in 6-well plates at a density of 2×10$^5$ cells/well in 2 ml DMEM supplemented with 100

IU/ml penicillin, 100 μg/ml streptomycin, and 10% fetal bovine serum (FBS) and cultured at 37° C. in humidified atmosphere containing 5% $CO_2$. After 24 hours incubation the cells reached 70~90% confluence and were followed by cell transduction analysis. Biotin-labelled test compounds were applied to cell cultures and incubated for 30 min at 37° C. and the translocation of the compounds were visualized with straptavidin-FITC (1:200 diluted). Thereafter, the cells were rinsed twice with D-PBS and harvested with Accutase™ (Innovative Cell Technologies, Inc. San Diego, Calif.) and resuspended in 0.5 ml D-PBS for FACS analysis. In flow cytometry analysis, 50,000 cells per sample were counted by the FACS Calibur, using Cell Quest software (BD Biosciences, Heidelberg, Germany). The mean of three separate measurements was determined. Seven test compounds were evaluated, including biotin-arg4 (SEQ ID NO: 7), biotin-arg6 (SEQ ID NO:8), biotin-arg8 (SEQ ID NO:9), biotin-arg4-ahx-arg4 (SEQ ID NO: 10), biotin-arg4-ahx2-arg4 (SEQ ID NO: 11), biotin-arg4-ahx3-arg4 (SEQ ID NO: 12), and biotin-arg4-ahx4-arg4 (SEQ ID NO: 13), where "arg" refers to arginine residues and "ahx" refers to aminohexanoic acid residues. The cell-penetrating activity of the test compounds is illustrated in FIG. 1. The data indicates that the novel divalant arginine compounds (biotin-arg4-ahx-arg4 (SEQ ID NO: 10), biotin-arg4-ahx2-arg4 (SEQ ID NO: 11), biotin-arg4-ahx3-arg4 (SEQ ID NO: 12), and biotin-arg4-ahx4-arg4 (SEQ ID NO: 13)) were similar in effectiveness to oligoarginine compounds.

Although the invention has been described with reference to embodiments and examples, it should be understood that numerous and various modifications can be made without departing from the spirit of the invention. Accordingly, the invention is limited only by the following claims.

What is claimed is:
1. A compound having the formula:
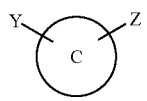
wherein C is selected from the group consisting of:
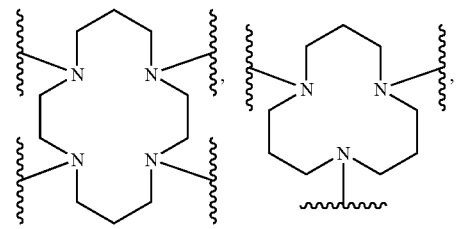
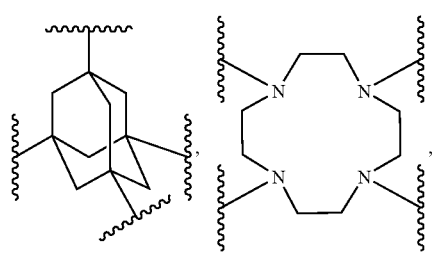
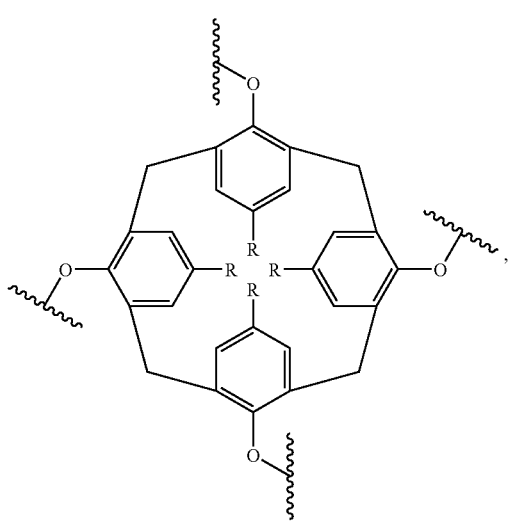
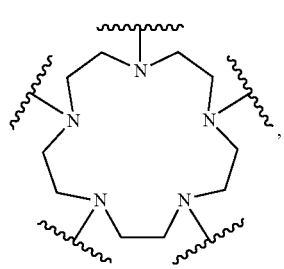
-continued
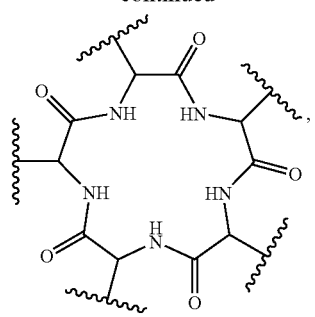
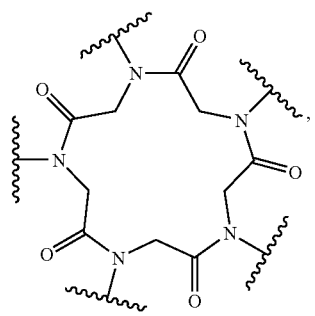
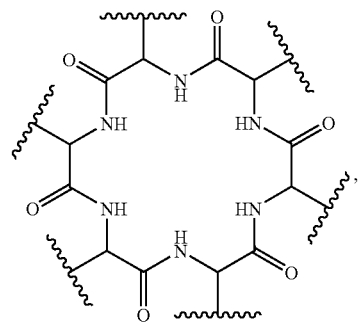
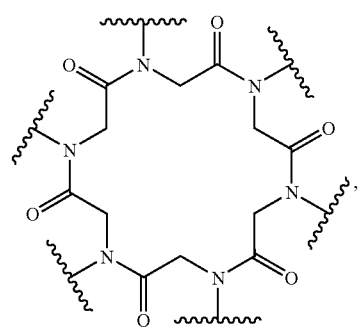
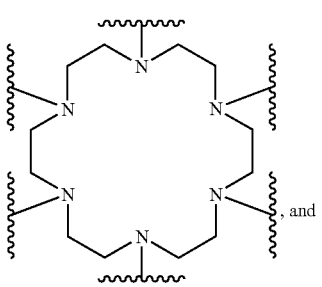

-continued

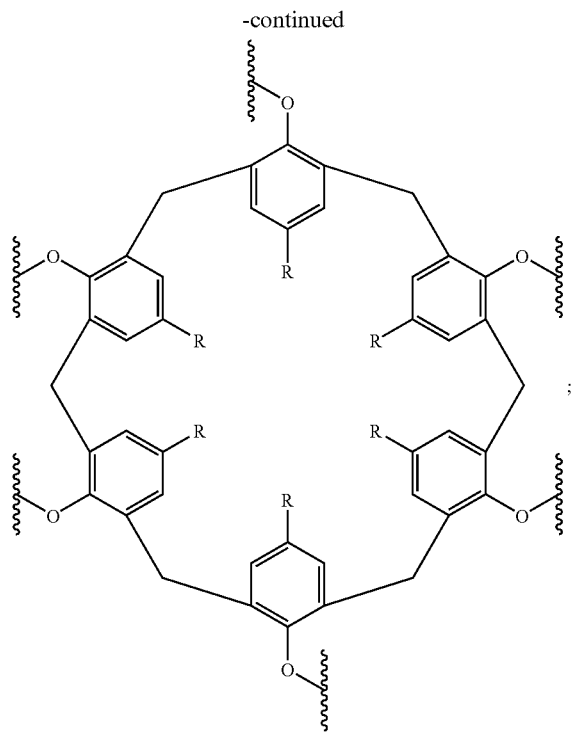

;

wherein R is selected from the group consisting of hydrogen, optionally substituted $C_{1-12}$ alkyl, optionally substituted $C_2$-$C_{12}$ alkenyl, and optionally substituted $C_2$-$C_{12}$ alkynyl;

wherein Y is a group of the formula:

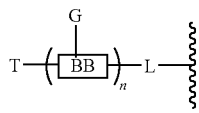

wherein 2 to 6 Y groups are attached to C;

wherein Z has the formula:

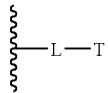

wherein one Z is attached to C or is absent;

wherein each L is separately selected to be a linker moiety comprising a molecular fragment having a molecular weight less than 1000;

wherein each BB is separately selected to be a backbone moiety comprising an organic fragment having a molecular weight less than 5000;

wherein each G is separately selected to be a guanidinium group covalently attached to BB and has the formula:

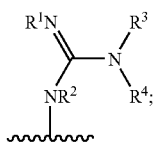

or each G is separately selected from the group consisting of:

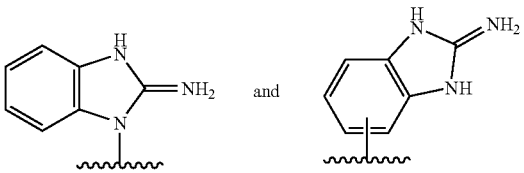

each $R^1$, $R^2$, $R^3$, and $R^4$ is hydrogen;

wherein each T is a terminal group separately selected from the group consisting of hydrogen, an amine group, a carboxylic group, a N-terminal peptide or group that forms an N-terminal peptide bond with BB, a C-terminal peptide or group that forms a C-terminal peptide bond with BB, a reporting moiety, a targeting moiety, and a therapeutic moiety, or each T is separately absent; and wherein each n is separately selected to be an integer from 1 to 8.

2. The compound of claim 1, wherein each L is separately selected from the group consisting of: —C(=O)NH—, —C(=O)NHO—, —C(=O)NHNH—, —S(=O)(=O)NR—, —P(=O)(—OR)NR'—, —SS—, —CH$_2$NR—, —CH$_2$NR—, —CH$_2$C(=O)NR—, —C(=O)O—, —C(=S)NR—, —S(=O)(=O)CH$_2$—, —SOCH$_2$— and —OC(=O)NR—, wherein each R and R' are separately selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl.

3. The compound of claim 1, wherein at least two Y groups attached to C are different from each other.

4. The compound of claim 1, wherein each BB-G is separately selected from the group consisting of:

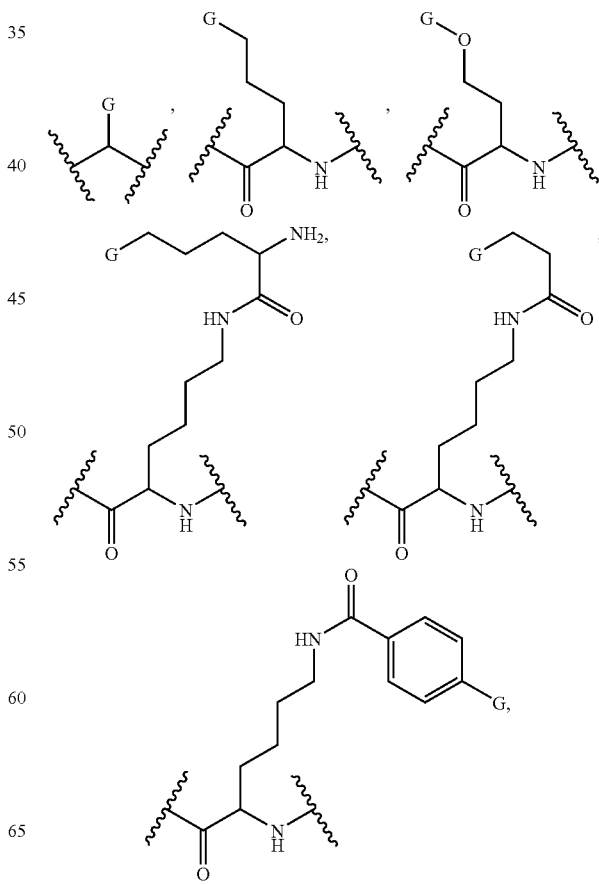

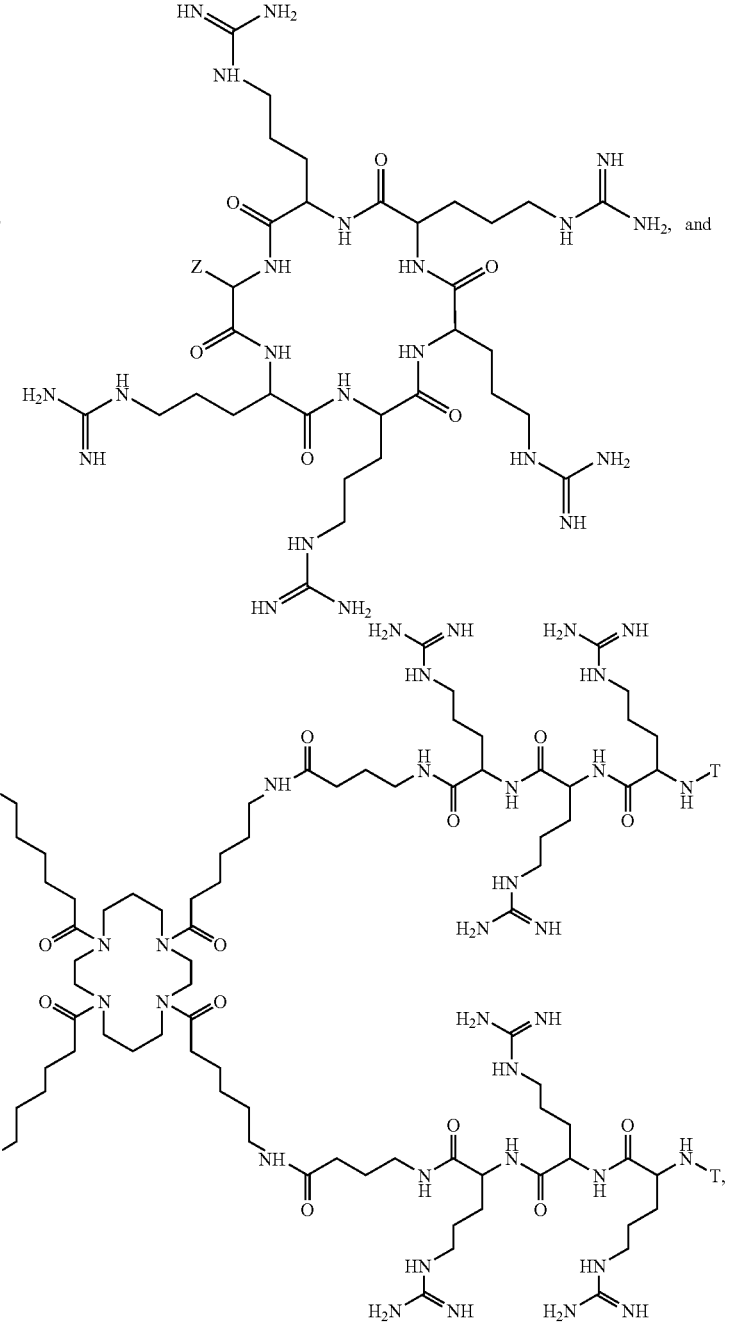

5. The compound of claim 1, wherein at least one T comprises a polypeptide.

6. The compound of claim 5, wherein at least one T comprises a protein antigen.

7. The compound of claim 6, wherein at least one T comprises a tumor antigen.

8. The compound of claim 1, wherein at least one T comprises an antimicrobial agent.

9. The compound of claim 1, wherein at least one T comprises a cleavable linker.

10. The compound of claim 9, wherein said cleavable linker comprises an ester group.

11. The compound of claim 9, wherein said cleavable linker comprises a disulfide group.

12. A compound selected from the group consisting of:

wherein Z has the formula:

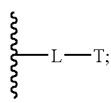

wherein each T is a terminal group separately selected from the group consisting of hydrogen, an amine group, a carboxylic group, a N-terminal peptide or group that forms an N-terminal peptide bond with BB, a C-terminal peptide or group that forms a C-terminal peptide bond with BB, a reporting moiety, a targeting moiety, and a therapeutic moiety, or each T is separately absent; and wherein each L is separately selected to be a linker moiety comprising a molecular fragment having a molecular weight less than 1000.

13. A method for enhancing transport of a biologically active moiety across a biological membrane, comprising contacting a biological membrane with a compound of claim 1, wherein at least one T comprises the biologically active moiety, whereby said contacting is effective to promote transport of said compound across said biological membrane at a rate that is greater than a trans-membrane transport rate of the biologically active moiety in non-conjugated form.

14. The method of claim 13, wherein said biological membrane is a eukaryotic cell membrane.

15. The method of claim 13, wherein said biological membrane is a prokaryotic cell membrane.

16. The method of claim 13, wherein said biological membrane is a cancer cell membrane.

17. The method of claim 13, wherein said biologically active moiety is a therapeutic moiety.

18. The method of claim 13, wherein said therapeutic moiety is an anti-cancer agent.

19. A pharmaceutical composition, comprising a compound of claim 1 and a pharmaceutically acceptable carrier, diluent, or excipient.

20. The compound of claim 12, wherein each L is separately selected from the group consisting of: an oligopeptide comprising 1 to 12 amino acid residues, an optionally substituted $C_1$-$C_{12}$ alkyl, an optionally substituted $C_2$-$C_{12}$ alkenyl, an optionally substituted $C_2$-$C_{12}$ alkynyl, and an optionally substituted $C_3$-$C_{12}$ cyclic alkyl, alkenyl, alkynyl, or aromatic moiety.

21. The compound of claim 12, wherein each L is separately selected from the group consisting of: —C(=O)NH—, —C(=O)NHO—, —C(=O)NHNH—, —S(=O)(=O)NR—, —P(=O)(—OR)NR'—, —SS—, —CH$_2$NR—, —CH$_2$NR—, —CH$_2$C(=O)NR—, —C(=O)O—, —C(=S)NR—, —S(=O)(=O)CH$_2$—, —SOCH$_2$— and —OC(=O)NR—, wherein each R and R' are separately selected from the group consisting of hydrogen, optionally substituted $C_1$-$C_{12}$ alkyl, optionally substituted $C_2$-$C_{12}$ alkenyl, and optionally substituted $C_2$-$C_{12}$ alkynyl.

22. The compound of claim 12, wherein each T is a terminal group separately selected from the group consisting of a reporting moiety, a targeting moiety, and a therapeutic moiety.

* * * * *

UNITED STATES PATENT AND TRADEMARK OFFICE
CERTIFICATE OF CORRECTION

PATENT NO. : 7,745,392 B2
APPLICATION NO. : 11/525512
DATED : June 29, 2010
INVENTOR(S) : Zheng Hou, Jian Liu and Lei Yu Page 1 of 2

It is certified that error appears in the above-identified patent and that said Letters Patent is hereby corrected as shown below:

At Column 9-10, Line 1-28 (Approx.), please delete

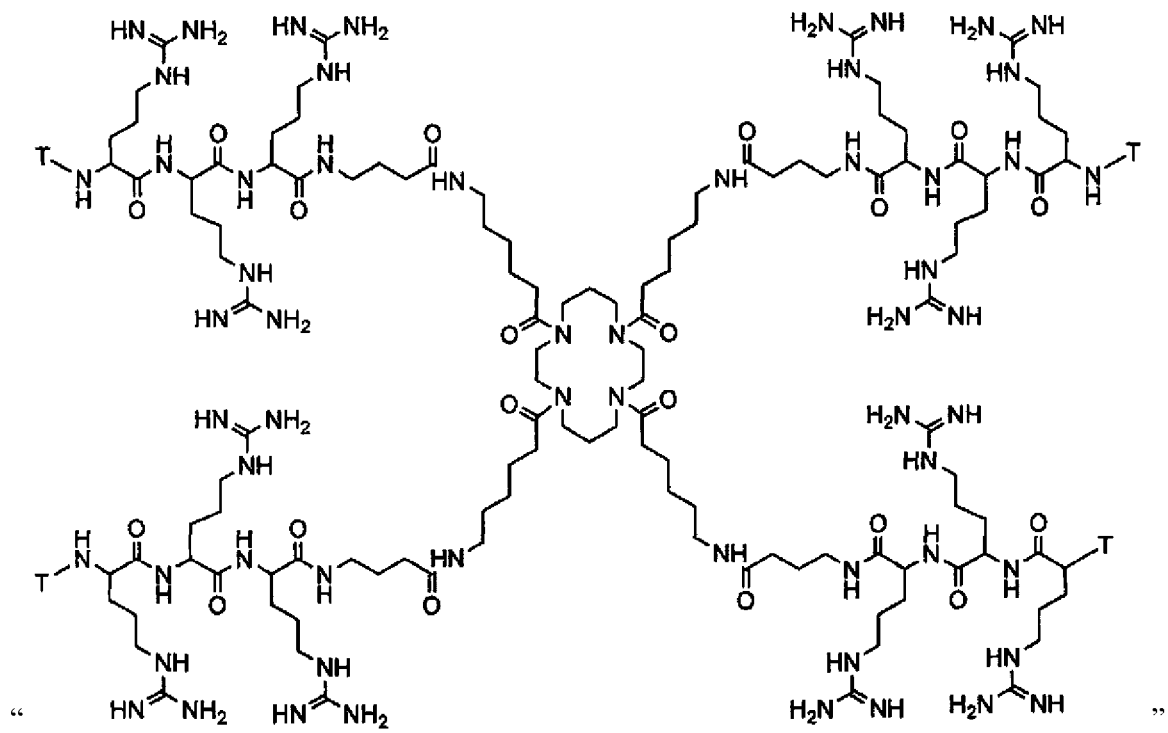

and insert

Signed and Sealed this
Twenty-sixth Day of February, 2013

Teresa Stanek Rea
*Acting Director of the United States Patent and Trademark Office*

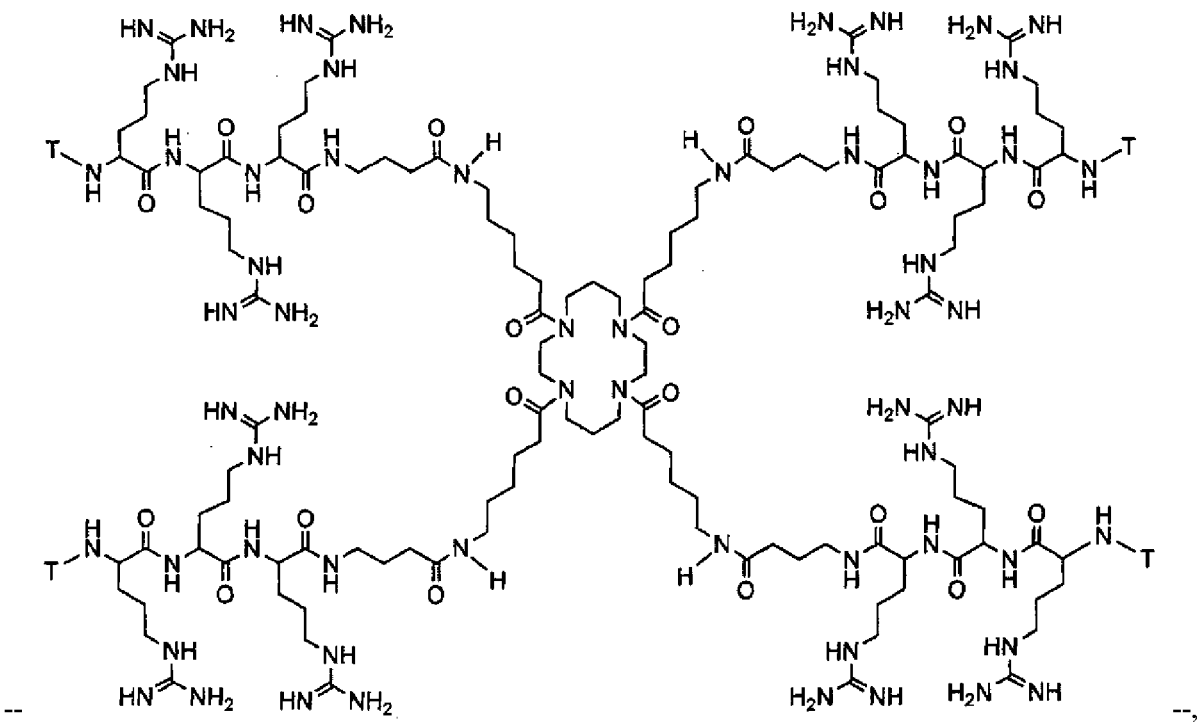

-- therefor;

At Column 29, Line 51, please delete "p-toluensulfonic" and insert --p-toluenesulfonic--, therefor;

At Column 30, line 64, please delete "cylcloalkenyl," and insert --cycloalkenyl,--, therefor;

At Column 37, Line 37, please delete "methasilicate" and insert --metasilicate--, therefor;

At Column 53, Line 8, please delete "straptavidin-FITC" and insert --streptavidin-FITC--, therefor;

At Column 54, Line 6, please delete "divalant" and insert --divalent--, therefor;

At Column 63, Line 32, In Claim 1, please delete "$C_{1-12}$" and insert --$C_1$-$C_{12}$--, therefor.

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetically created protected tetrapeptide
<220> FEATURE:
<221> NAME/KEY: MOD_RES
<222> LOCATION: 1
<223> OTHER INFORMATION: Xaa = Btn-Arg (Pmc)
<220> FEATURE:
<221> NAME/KEY: MOD_RES
<222> LOCATION: (2)...(3)
<223> OTHER INFORMATION: Xaa = Arg (Pmc)
<220> FEATURE:
<221> NAME/KEY: MOD_RES
<222> LOCATION: 4
<223> OTHER INFORMATION: Xaa = 4Abu

<400> SEQUENCE: 1

Xaa Xaa Xaa Xaa
 1

<210> SEQ ID NO 2
<211> LENGTH: 8
<212> TYPE: PRT
<213> ORGANISM: Artificial Sequence
<220> FEATURE:
<223> OTHER INFORMATION: Synthetically created protected heptaarginine
      octapeptide
<220> FEATURE:
<221> NAME/KEY: MOD_RES
<222> LOCATION: (1)...(7)
<223> OTHER INFORMATION: Xaa = Arg (Pmc)
<220> FEATURE:
<221> NAME/KEY: MOD_RES
<222> LOCATION: 8
<223> OTHER INFORMATION: Xaa = Asp (HMPA-PEGA)-OAllyl

<400> SEQUENCE: 2

Xaa Xaa Xaa Xaa Xaa Xaa Xaa Xaa
 1               5

<210> SEQ ID NO 3
<211> LENGTH: 9
<212> TYPE: PRT
<213> ORGANISM: Artificial Sequence
```

```
<220> FEATURE:
<223> OTHER INFORMATION: Synthetically created protected heptaarginine
      nonapeptide
<220> FEATURE:
<221> NAME/KEY: MOD_RES
<222> LOCATION: 1
<223> OTHER INFORMATION: Xaa = Trt-Cys(Xan)
<220> FEATURE:
<221> NAME/KEY: MOD_RES
<222> LOCATION: 2-8
<223> OTHER INFORMATION: Xaa = Arg (Pmc)
<220> FEATURE:
<221> NAME/KEY: MOD_RES
<222> LOCATION: 9
<223> OTHER INFORMATION: Xaa = Asp (HMPA-PEGA)-OAllyl

<400> SEQUENCE: 3

Xaa Xaa Xaa Xaa Xaa Xaa Xaa Xaa Xaa
 1               5

<210> SEQ ID NO 4
<211> LENGTH: 9
<212> TYPE: PRT
<213> ORGANISM: Artificial Sequence
<220> FEATURE:
<223> OTHER INFORMATION: Synthetically created protected heptaarginine
      nonapeptide
<220> FEATURE:
<221> NAME/KEY: MOD_RES
<222> LOCATION: 1
<223> OTHER INFORMATION: Xaa = Trt-Cys(Xan)
<220> FEATURE:
<221> NAME/KEY: MOD_RES
<222> LOCATION: 2-8
<223> OTHER INFORMATION: Xaa = Arg (Pmc)
<220> FEATURE:
<221> NAME/KEY: MOD_RES
<222> LOCATION: 9
<223> OTHER INFORMATION: Xaa = Asp (HMPA-PEGA)-OH

<400> SEQUENCE: 4

Xaa Xaa Xaa Xaa Xaa Xaa Xaa Xaa Xaa
 1               5

<210> SEQ ID NO 5
<211> LENGTH: 10
<212> TYPE: PRT
<213> ORGANISM: Artificial Sequence
<220> FEATURE:
<223> OTHER INFORMATION: Synthetically created protected heptaarginine
      decapeptide
<220> FEATURE:
<221> NAME/KEY: MOD_RES
<222> LOCATION: 1
<223> OTHER INFORMATION: Xaa = Trt-Cys(Xan)
<220> FEATURE:
<221> NAME/KEY: MOD_RES
<222> LOCATION: 2-8
<223> OTHER INFORMATION: Xaa = Arg (Pmc)
<220> FEATURE:
<221> NAME/KEY: MOD_RES
<222> LOCATION: 9
<223> OTHER INFORMATION: Xaa = Asp (HMPA-PEGA)
<220> FEATURE:
<221> NAME/KEY: MOD_RES
<222> LOCATION: 10
<223> OTHER INFORMATION: Xaa = Phe-SBz

<400> SEQUENCE: 5

Xaa Xaa Xaa Xaa Xaa Xaa Xaa Xaa Xaa Xaa
 1               5                  10
```

```
<210> SEQ ID NO 6
<211> LENGTH: 10
<212> TYPE: PRT
<213> ORGANISM: Artificial Sequence
<220> FEATURE:
<223> OTHER INFORMATION: Synthetically created cyclic heptaarginine
      decapeptide

<400> SEQUENCE: 6

Cys Arg Arg Arg Arg Arg Arg Arg Asp Phe
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetically created biotinylated
      tetraarginine
<220> FEATURE:
<221> NAME/KEY: MOD_RES
<222> LOCATION: 1
<223> OTHER INFORMATION: Xaa = Biotin-Arg

<400> SEQUENCE: 7

Xaa Arg Arg Arg
1

<210> SEQ ID NO 8
<211> LENGTH: 6
<212> TYPE: PRT
<213> ORGANISM: Artificial Sequence
<220> FEATURE:
<223> OTHER INFORMATION: Synthetically created biotinylated Hexaarginine
<220> FEATURE:
<221> NAME/KEY: MOD_RES
<222> LOCATION: 1
<223> OTHER INFORMATION: Xaa = Biotin-Arg

<400> SEQUENCE: 8

Xaa Arg Arg Arg Arg Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetically created biotinylated octaarginine
<220> FEATURE:
<221> NAME/KEY: MOD_RES
<222> LOCATION: 1
<223> OTHER INFORMATION: Xaa = Biotin-Arg

<400> SEQUENCE: 9

Xaa Arg Arg Arg Arg Arg Arg Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetically created biotinylated octaarginine
      nonapeptide
<220> FEATURE:
<221> NAME/KEY: MOD_RES
<222> LOCATION: 1
<223> OTHER INFORMATION: Xaa = Biotin-Arg
```

```
<220> FEATURE:
<221> NAME/KEY: MOD_RES
<222> LOCATION: 5
<223> OTHER INFORMATION: Xaa = Acp

<400> SEQUENCE: 10

Xaa Arg Arg Arg Xaa Arg Arg Arg
 1               5

<210> SEQ ID NO 11
<211> LENGTH: 10
<212> TYPE: PRT
<213> ORGANISM: Artificial Sequence
<220> FEATURE:
<223> OTHER INFORMATION: Synthetically created biotinylated octaarginine
      decapeptide
<220> FEATURE:
<221> NAME/KEY: MOD_RES
<222> LOCATION: 1
<223> OTHER INFORMATION: Xaa = Biotin-Arg
<220> FEATURE:
<221> NAME/KEY: MOD_RES
<222> LOCATION: 5-6
<223> OTHER INFORMATION: Xaa = Acp

<400> SEQUENCE: 11

Xaa Arg Arg Arg Xaa Xaa Arg Arg Arg Arg
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Synthetically created biotinylated octaarginine
      undecapeptide
<220> FEATURE:
<221> NAME/KEY: MOD_RES
<222> LOCATION: 1
<223> OTHER INFORMATION: Xaa = Biotin-Arg
<220> FEATURE:
<221> NAME/KEY: MOD_RES
<222> LOCATION: 5-7
<223> OTHER INFORMATION: Xaa = Acp

<400> SEQUENCE: 12

Xaa Arg Arg Arg Xaa Xaa Xaa Arg Arg Arg Arg
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Synthetically created biotinylated octaarginine
      dodecapeptide
<220> FEATURE:
<221> NAME/KEY: MOD_RES
<222> LOCATION: 1
<223> OTHER INFORMATION: Xaa = Biotin-Arg
<220> FEATURE:
<221> NAME/KEY: MOD_RES
<222> LOCATION: 5-8
<223> OTHER INFORMATION: Xaa = Acp

<400> SEQUENCE: 13

Xaa Arg Arg Arg Xaa Xaa Xaa Xaa Arg Arg Arg Arg
 1               5                  10
```